United States Patent [19]
Casagrande et al.

[11] Patent Number: 5,468,746
[45] Date of Patent: Nov. 21, 1995

[54] COMPOUNDS ACTIVE ON THE CARDIOVASCULAR SYSTEM

[75] Inventors: Cesare Casagrande, Arese; Stefania Montanari; Francesco Santangelo, both of Milan, all of Italy

[73] Assignee: Zambon Group S.p.A., Vicenza, Italy

[21] Appl. No.: 719,103

[22] Filed: Jun. 21, 1991

Related U.S. Application Data

[63] Continuation of Ser. No. 386,236, Jul. 28, 1989, abandoned.

[30] Foreign Application Priority Data

Jul. 29, 1988 [IT] Italy ............................. 21541
Jul. 29, 1988 [IT] Italy ............................. 21542

[51] Int. Cl.$^6$ .................... A61K 31/535; C07D 401/06; C07D 405/06; C07D 417/06
[52] U.S. Cl. .................... 514/235.5; 514/336; 514/337; 514/338; 514/339; 514/342; 546/269; 546/273; 546/277; 546/321; 544/124
[58] Field of Search .................... 546/269, 273, 546/277, 321; 544/124; 514/235.5, 336, 337, 338, 339, 342

[56] References Cited

FOREIGN PATENT DOCUMENTS 0194752 9/1986 European Pat. Off. .
0218068 4/1987 European Pat. Off. .
8604581 8/1986 WIPO ........................... C07D 211/90

Primary Examiner—Gollamudi S. Kishore
Attorney, Agent, or Firm—Jacobson, Price, Holman & Stern

[57] ABSTRACT

Compounds of the formula

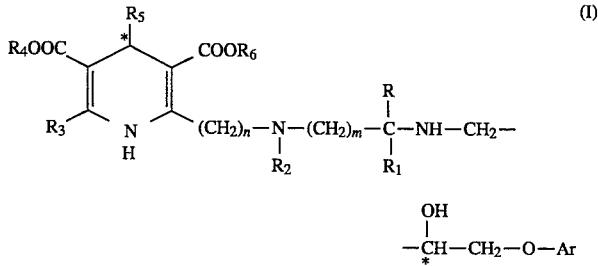

(wherein Ar, R, $R_1$, $R_2$, $R_3$, $R_4$, $R_5$, m and n have the meanings given in the description), their preparation and pharmaceutical compositions containing them.

The compounds of formula I are active on the cardiovascular system as antivasospastics, antiangina agents, antihypertensives and vasodilators.

19 Claims, No Drawings

COMPOUNDS ACTIVE ON THE CARDIOVASCULAR SYSTEM

This application is a continuation of U.S. Ser. No. 07/386,236, filed Jul. 28, 1987, now abandoned.

The present invention relates to compounds active on the cardiovascular system; more particularly, it relates to compounds having a dihydropyridine nucleus, pharmaceutically acceptable salts thereof, processes for preparing them and pharmaceutical compositions containing them.

Compounds having calcium-antagonist properties and 4-aryldihydropyridine structure are known; their typical representative is 4-(2-nitrophenyl)-2,6-dimethyl-3,5-dimethoxcarbonyl- 1,4-dihydropyridine known as Nifepidine (Merck Index 10th Ed., No. 6374) of the formula

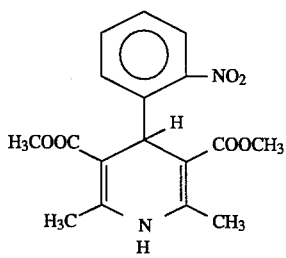
(A)

Beta-blocking drugs are also known and widely used in therapy for treating cardiovascular diseases. In most cases these drugs are structurally related to 3-aryloxy-2-hydroxy-propan-amines.

Examples of beta-blockers most commonly used in therapy, mainly as antihypertensives, include Alprenolol (Merck Index, X ed., No. 304), Atenolol (Merck Index, X ed., No. 868), Carteolol (Merck Index, X ed., No. 1850), Metoprolol (Merck Index, X ed., No. 6027), Nadolol (Merck Index, X ed., No. 6195), Oxprenol (Merck Index, X ed., No. 6820), Pindolol (Merck Index, X ed., No. 7317), Propanolol (Merck Index, X ed., No. 7740), and Timolol (Merck Index, X ed., No. 9284).

Furthermore, some compounds have been described wherein the 3-aryloxy-2-hydroxy-propanamine moiety of beta-blockers is linked at different positions of the 4-aryl-dihydropyridine moiety endowed with calcium-antagonist activity.

Baldwin J. J. et al., J. Med. Chem., 1981, 24 628–631 discloses compounds wherein the beta-blocker chain is linked to the aryl moiety of 4-aryl-dihydropyridine at position 4, but these compounds resulted scarcely active; European Patent Application No. 179386 (Bayer A. G.) describes compounds wherein the beta-blocker chain is linked at the carboxy group at position 3 of the 4-aryl-dihydropyridine.

Now we have found a novel class of compounds wherein both a typical beta-blocker structure and a calcium-antagonist moiety are suitably interconnected and show a remarkable antihypertensives activity.

It is therefore an object of this invention to provide a compound of the formula:

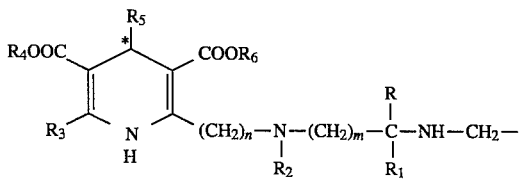
(I)

-continued

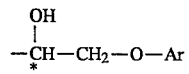

wherein

Ar is a mono- or dicyclo aromatic or heteroaromatic ring system having from 5 to 10 atoms in the aromatic nucleus optionally substituted by one or more substituents selected from halogen, hydroxy, $C_1$–$C_5$ alkyl, $C_2$–$C_5$ alkenyl, $C_1$–$C_3$ alkoxy, alkoxyalkyl having from 1 to 5 carbon atoms both in the alkyl and in the alkoxy moiety and an optional unsaturation in the chain, phenoxy, phenylalkoxy, aminocarbonylalkyl having from 1 to 3 carbon atoms in the alkyl moiety, cyano, carboxy, carbamoylalkyl, aminocarboxy, amino, mono- and di-alkylamino where the nitrogen atom may be a part of a ring;

R and $R_1$, the same or different, are hydrogen or $C_1$–$C_3$ alkyl;

$R_2$ is a straight or branched $C_1$–$C_7$ alkyl or a straight or branched $C_2$–$C_7$ alkenyl optionally substituted by aryl, additionally $R_2$ may be X-$R_7$ where X is CO, CS or $SO_2$ and $R_7$ is an alkyl or an alkoxyalkyl having from 1 to 5 carbon atoms both in the alkyl and the alkoxy moiety, hydroxy, $C_1$–$C_3$ alkoxy, mono- or di-alkylamino having from 1 to 5 carbon atoms in the alkyl moiety, or $C_1$–$C_5$ alkylthio;

$R_3$ is cyano, amino or $C_1$–$C_3$ alkyl optionally substituted by fluorine atoms;

$R_4$ and $R_6$, the same or different, are alkyl or alkoxyalkyl having from 1 to 5 carbon atoms both in the alkyl and alkoxy moiety;

$R_5$ is a ring selected from phenyl, naphthyl, tetrahydronaphthyl and indanyl, wherein said ring may be substituted by one or more substituents selected from halogen, hydroxy, alkyl, alkenyl, alkoxy, alkenyloxy, alkoxyalkyl, alkanoyl, trifluoromethyl, amino, nitro, carbamoyl, cyano, alkylthio, carbamoylalkyl and alkanoylamino having up to 6 carbon atoms in the alkyl moiety;

m and n, the same or different, are 1, 2 or 3; and the salts thereof with organic or inorganic pharmaceutically acceptable acids.

The compounds of formula I have at least two asymmetric carbon atoms and can therefore exist as stereoisomers.

Another object of this invention is to provide the compounds of formula I both as stereoisomeric mixtures and as single stereoisomers.

The single stereoisomers are obtained by stereoselective synthesis or by separation from the stereoisomeric mixture according to such known techniques as fractional crystallization, chromatography and resolution by means of salification or preparation of derivatives with optically active compounds.

The salts of the compounds of this invention with pharmaceutically acceptable organic and inorganic acids are prepared according to conventional methods.

Examples of pharmaceutically acceptable acids are hydrochloric, hydrobromic, phosphoric, sulfuric, lactic, succinic, tartaric, acetic, salicyclic, citric, benzoic, p-hydroxybenzoic, naphthalene-2-sulfonic, adipic and pimelic acid.

The compounds of formula I and their pharmaceutically acceptable salts are active on the cardiovascular system as antivasospastics, antiangina agents, antihypertensives and vasodilators.

Unless otherwise stated, when used in connection with R, $R_1$, $R_2$, $R_3$, $R_4$, $R_5$, $R_6$, $R_7$ and Ar, alkyl means a straight or branched alkyl having, preferably, from 1 to 6 carbon atoms (typical examples being methyl, ethyl, n-propyl, 1-propyl, n-butyl, sec-butyl, tert-butyl, n-pentyl and n-hexyl); the alkyl moiety of alkoxy and alkoxyalkyl is intended to have the meaning cited above for alkyl; aryl and aromatic or heteroaromatic system mean an aromatic or heteroaromatic nucleus having 5 (heteroaromatic), 6, 9, 10 or 12 members and the heteroaromatic nucleus may have from 1 to 3 heteroatoms selected from oxygen, sulfur and nitrogen (typical examples being furyl, pyrrolyl, isoxazolyl, 1,2,5-triazolyl, oxazolyl, phenyl, pyridyl, indenyl, indolyl, naphthyl, benzofuranyl, isobenzofuranyl, quinolyl, diphenyl and phenylipyridyl); alkenyl means a branched or straight alkenyl radical having from 2 to 7 carbon atoms and at least one unsaturation (typical examples being vinyl, allyl, 2,2-dimethylvinyl, and 1-butadienyl); alkanoyl means a residue of a straight or branched carboxylic acid having 1 to 5 carbon atoms (typical examples being formyl, aceyl, butyroyl and isobutyroyl).

A preferred group of compounds of formula I includes those compounds wherein Ar has the same meaning as the aryl group in known beta-blockers.

Preferred meanings of Ar comprise phenyl, naphthyl, isobenzofuranyl, benzofuranyl, 3,4-dihydrocarbostyryl, benzopyranyl, tetrahydronaphthyl, carbazolyl, indeny, indolyl and 1,2,5-thiadiazolyl, optionally substituted.

Examples of possible substituents comprise one or more fluorine, chlorine, bromine, acetyl, allyl, carbamoylmethyl, butyroylamino, cyclohexyl, cyano, hydroxy, butyroyl, acetylamino, methoxycarbonyl, methoxyethyl, methoxy, allyloxy, cyclopentyl, cyclopropyl, morpholine, ethyl and isobutyroyl.

Specific examples of preferred substituted aryls comprise 2-methoxyphenyl, 2-allyloxyphenyl, 2-cyanophenyl, 2-methylphenyl, 2-allylphenyl, 4-carbamoylmethylphenyl, 4-hydroxyphenyl, 4-morpholino-1,2,5-thiadiazol-3-yl, indol-4-yl and 3,4-dihydro- 1-(H)-carbostyryl-5-yl.

Another group of preferred compounds includes those compounds wherein $R_5$ is a substituted phenyl and more particularly 3-nitrophenyl, 2-nitrophenyl, 2-chlorophenyl, 2-trifluoromethyl-phenyl, and 2,3-dichlorophenyl.

A third group of preferred compounds includes those compounds wherein R and $R_1$, the same or different, are hydrogen or methyl.

A fourth group of preferred compounds comprises those compounds wherein $R_3$ is methyl or trifluoromethyl.

Finally, among the compounds of general formula I a group of most preferred compounds comprises the compounds wherein Ar is selected from 2-methoxyphenyl, 2-allyloxyphenyl, 2-cyanophenyl, 2-methylphenyl, 2-allylphenyl, 4-carbamoylmethylphenyl, 4-hydroxyphenyl, 4-morpholino-1,2,5-thiadiazol- 3-yl, indol-4-yl and 3,4-dihydro-1(H)-carbostyryl- 5-yl;

R and $R_1$, the same or different, are hydrogen or methyl;

$R_2$ has the meanings mentioned above in connection with formula I;

$R_3$ is methyl or trifluoromethyl;

$R_4$ and $R_6$ have the meanings mentioned above in connection with formula I;

$R_5$ is phenyl substituted by one or more substituents selected from nitro, trifluoromethyl and halogen;

X is a carbonyl or sulfonic group.

$R_7$ is methyl, ethyl, isopropyl, phenyl, dimethylamino, diethylamino, methoxy or ethoxy.

A further object of this invention is to provide a process for preparing a compound of formula I comprising (i) the condensation of the $R_2$—NH— group of a diamine of the formula

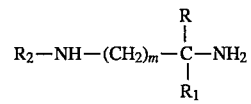

wherein R, $R_1$, and m have the meanings mentioned above in connection with formula I and $R_2$ is a member selected from alkyl and alkenyl, wherein both members, straight or branched, have from 1 to 7 carbon atoms and are optionally substituted by an aryl group;

with a 2-alkylen-4-aryl-dihydropyridine and (ii) the introduction of a 3-aryloxy-2-hydroxy-propyl radical on the primary amino group of (II).

Both steps can be performed according to several procedures and step (ii) may also precede step (i).

In the following description of the synthesis method R, $R_1$, $R_3$, $R_4$, $R_5$, $R_6$, Ar, m and n have the meanings already mentioned above in relation to formula I, R2 has the meanings already mentioned above in relation to formula II.

Before performing step (i), the primary amino group of diamine II is preferably protected according to conventional techniques. Examples of suitable protective groups comprise benzyl, benzyloxycarbonyl, ter.butyloxycarbonyl and phthalimido group.

Step (i) affords, after condensation of a 2-alkylen-4-aryl-dihydropyridine compound with a protected diamine (II) and subsequent removal of the protecting group, a compound of formula

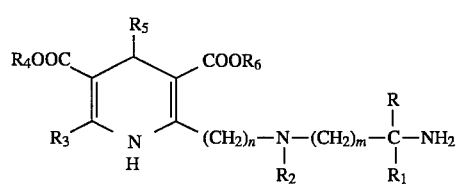

Step (ii) involves condensation of the compound (III) with an epoxide (IV) or with a compound of formula or (V)

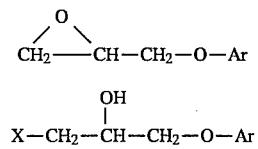

wherein X is halogen, alkyl or arylsulfonyloxy, to afford a compound of formula I.

A preferred way of performing step (i) comprises the condensation of a protected diamine (II) with a 2-alkylene-4-aryl-dihydropyridine compound of formula

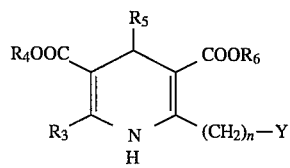

wherein Y is a leaving group.

Examples of preferred leaving groups comprise chlorine, bromine, iodine, alkylsulfonyloxy, and arylsulfonyloxy. Typical examples of preferred leaving groups are methanesulfonyloxy, benzenesulfonyloxy and p-toluenesulfonyloxy.

The condensation of compound (IV) with a protected diamine (II) is performed in an inert solvent and in the presence of a base.

After preferred way of performing step (i) comprises the condensation of a protected diamine (II) with a 2-alkylen-4-aryl-dihydropyridine compound of the formula t,100

The condensation of compound (VII) with a protected diamine (II) is performed in an inert solvent, optionally in the presence of a dehydrating agent, and subsequent reduction. This reduction is preferably carried out by catalytic hydrogenolysis or with reducing agents, such as sodium boron hydride and sodium cyano hydride.

When step (ii) is carried out before step (i), the diamine (II) is optionally protected on the secondary amino group ($R_2$—NH—), the optionally protected diamine (II) is then reacted with a compound of formula (IV) or (V) to give, after removal of the possible protective group, a compound of the formula

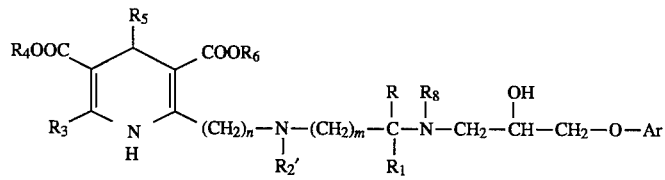

and finally the compound (VIII), is reached with a compound of formula (VI) or (VII).

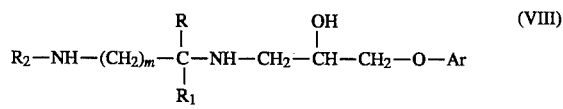

Protection and removal of the protective group are carried out as described above.

The condensation reaction of the optionally protected diamine (II) with a compound of formula (IV) or (V) is also performed as described above in connection with the reaction of compound (III) with compounds (IV) or (V).

Even the reaction of compounds (VIII) with compound (VI) or (VII) is carried out as described above.

Another way for performing step (ii) before step (i) comprises preparing a compound of the formula

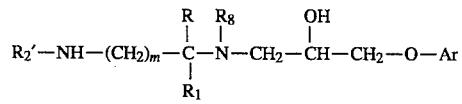

wherein $R_2'$ is hydrogen or a member selected from alkyl and alkenyl wherein both members, straight or branched, have from 1 to 7 carbon atoms and are optionally substituted by an aryl group; and $R_8$ is a protective group; by reacting an amide of the formula

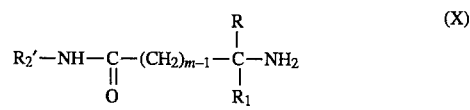

with a compound of formula (IV) or (V) to give a compound of the formula

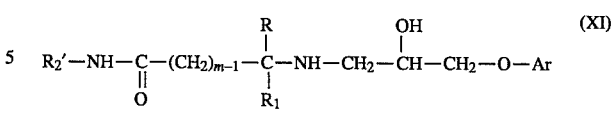

which is then protected by a protective agent and reduced to afford a compound of formula (IX).

The preferred meaning of $R_8$ is trifluoromethyl.

Reduction is preferably carried out with hydrides, such as lithium aluminum hydride, lithium boron hydride, cobalt boron hydride and borane.

Another way of performing step (i) comprises the reaction of a compound of formula (IX) with a compound of formula (VI) or (VII) to give a compound of the formula (XII)

This reaction is carried out as described above in relation to the preparation of compound (III).

When $R_2'$ is a member selected from alkyl and alkenyl, wherein both members, straight or branched, have from 1 to 7 carbon atoms and are optionally substituted by an aryl group, the compound of formula I can be easily prepared by simple removal of the protective group from compound (XII) according to conventional techniques, such as, a treatment with an acid.

When $R'_2$ is hydrogen, the compound of formula I is prepared by alkylation or acylation of compound (XII) and subsequent removal of the protective group.

The alkylation is carried out in an inert solvent and in the presence of a base with an alkylating agent of the formula $$R_2\text{—X'} \qquad \text{(XIII)}$$

where X' is chlorine or bromine; or with methyl sulfate.

Reacting a compound of formula (XII), wherein $R_2'$ is hydrogen, with suitable reactive derivatives of a carboxylic or a sulfonic acids, such as chlorides and anhydrides, or of carbonic acids, such as chlorocarbonates and chlorocarbamates; with isocyanates or isothiocyanates and subsequent removal of the protective group according to conventional methods, the compounds of formula I wherein $R_2$ is X—$R_7$ are obtained.

The condensation reaction is carried out in a suitable inert solvent, optionally in the presence of an organic or inorganic base as acid acceptor, at a temperature of from 0° C. to the reflux temperature of the reaction mixture.

Examples of suitable solvents comprise hydrocarbons, such as toluene and cyclohexane; ethers, such as tetrahydrofuran and dioxane; chlorinated hydrocarbons, such as dichloromethane, chloroform and tetrachloroethylene.

Examples of suitable bases comprise inorganic bases, such as alkali and alkaline-earth metals hydroxydes; bicarbonates and carbonates; and organic base, such as triethylamine and pyridine, which can also act as a solvent.

Preferred bases are sodium and potassium hydroxides, bicarbonates and carbonates.

The process of this invention contemplates also the protection of the amino group via formation of a heterocyclic ring, such as the conversion of compound (XI) to an oxazolidine compound of the formula

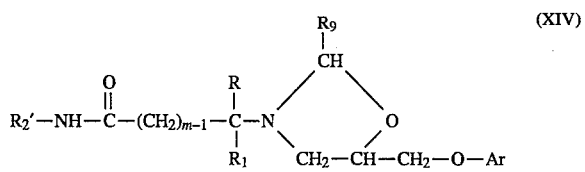

(XIV)

wherein $R_9$ is $C_1$-$C_6$ alkyl or phenyl.

Compounds of formula (XIV) are prepared by reacting a compound (XI), wherein the nitrogen atom linked to $R_2'$ is protected, or a compound (XI) where $R_2'$ is $R_2$, with an aldehyde of the formula $$R_9\text{—CHO} \qquad\qquad (XV)$$

At the end of the process, the oxazolidine ring is opened by treatment with acids and the hydroxy group is thus restored.

The compounds of formula I of this invention have at least two asymmetry centers which are marked by an asterisk.

The asymmetric synthesis for preparing diastereoselectively the compounds of formula I can be performed, for example, via optically active intermediate compounds of formula (III), (IV), (V), (VI), (VII) or (IX).

The compounds of formula (VI) and (VII) are known, for example, from European Patent Applications 109 009 and 212 340 or can be easily prepared according to the Hantszch method by reacting the compounds of formula $R_5$—CHO (XVI) and $R_3$—C($NH_2$)=CH—$COOR_4$ (XVII) and a keto ester of formula $R_6OOC$—$CH_2$—CO—$(CH_2)_{n-1}$—$R_{10}$ (XVIII) wherein $R_{10}$ is —$CH_2$—Y or —CHO or any other similar group, such as —$CH_2OH$.

The compounds of formula I proved be useful in the treatment of cardiovascular pathologies as anti-vasospastics, antiangina agents, antihypertensives and vasodilators.

The pharmacological activity of the compounds of this invention has been tested both in vitro and in vivo (Example 16).

The compounds of formula I are endowed with a remarkable calcium antagonist and beta blocking action and are useful in producing antihypertensive effects with concomitant reduction of heart rate, contrary to known calcium-antagonists in which the hypotensive effect is accompanied by tachycardia.

In addition to a remarkable action on the cardiovascular system, the compounds of formula I show interesting properties which make them particularly suitable for use in the pharmaceutical field.

Contrary to the known drugs having a dihydropyridine structure, the compounds of formula I have a considerable chemical and physical stability.

A still further object of the present invention is to provide a pharmaceutical composition containing a compound of formula I or a pharmaceutically acceptable salt thereof together with one or more solid or liquid, organic or inorganic pharmaceutical excipients, such as diluents, preservatives, humectants, dyes, flavours and the like.

The pharmaceutical compositions of the present invention may be administered as solid dosage forms, such as tablets, pills, capsules, granules and suppositories, or an liquid dosage forms, such as syrups, suspensions, emulsions and solutions suitable for oral or parenteral administration, or also as dosage forms suitable for transdermal administration, such as wax plasters.

The compounds of the present invention may also be compounded in slow releasing dosage forms.

The preparation of the pharmaceutical compositions of the present invention is carried out according to conventional techniques.

The doses of the compound of formula I will vary according to several factors, such as the specific activity of the single compound of formula I, the therapy and the individual patient response as well as the selected administration route.

Generally the amount of the compound of formula I to be administered will be in the range of from 0.1 mg to 200 mg per day in one or more repeated doses.

For the purpose of better illustrating the present invention, the following examples are now given.

EXAMPLE 1

Preparation of ethyl
1,4-dihydro-6-methyl-2-(N-methyl-N-(2-(2-hydroxy-
3-(2-methoxyphenoxy)-propylamino)-2-methyloropyl)
aminomethyl)-
4-(3-nitrophenyl)-3,5-pyridinedicarboxylate (Compound 1)

A mixture of ethyl 1,4-dihydro-2-formyl-6-methyl-4-(3-nitrophenyl)- 3,5-pyridinedicaboxylate (5.0 g; 13 mmoles), and of N-methyl-2-(2-hydroxy-3-(2-methoxyphenoxy)-propylamino)-2-methylpropylamine (3.65 g; 13 mmoles) in 95% ethanol (70 ml) is stirred for one hour at room temperature.

After cooling to 0°–5° C., water (31.8 ml), acetic acid (10.9 ml), sodium acetate (3.45 g) and finally sodium boron hydride (2.55 g; 70 mmoles) are added. The mixture is left for four hours at room temperature. After solvent evaporation, water is added to the residue which is basified with dilute ammonia and extracted with methylene chlorie.

The organic phase is dried over sodium sulfate and after evaporation of the solvent the residue is purified by chromatography on a silica gel column (230–400 mesh), eluting with methylene chloride and increasing amounts of ethanol up to a 95:5 ratio.

Ethyl 1,4-dihydro-6-methyl-2-(N-methyl-N-(2-(2-hydroxy- 3-(2-methoxyphenoxy)-propylamino)-2-methyloropyl)-aminomethyl)- 4-(3-nitrophenyl)-3,5-pyridinedicarboxylate is obtained as 1:1 mixture of the two diastereomer pairs (thin layer chromatography—eluent ethyl acetate:$NH_4OH$=99.1).

The two diastereomeric pairs had Rf=0.22 and Rf=0.17, respectively.

$^1$H-NMR diastereomeric mixture—free base (300 MHz, $CDCl_3$) delta (ppm); 1.18 (6H, 4s); 1,22 (6H, 2t); 2.40 (6H, s); 2.59 (2, m); 3.84 (3H, 2s); 3.93 (2H, m); 5.09 (1H, s); 7.35 (1H, 2t); 7.62 (1H, d); 7.98 (1H, d); 8.12 (1H bs).

The signal at 7.35 ppm is splitted because of the presence of two diastereoisomers and become simple in the spectra of the two pure diatereooisomers.

The two diastereoisomers were separated by chromatography on a silica gel column (230–400 mesh) eluting with ethylacetate; $NH_4OH$=99:1.

The less polar product is salified with a solution of hydrochloric acid in ether to give a crystalline hydrochloride salt melting at 116°–118° C. (ethyl acetate).

EXAMPLE 2

Preparation of methyl 1,4-dihydro-6-methyl-4-(3-nitrophenyl)-2-(2-oxo-ethyl)-3,5-pyridinedicarboxilate A solution of methyl 1,4-dihydro-2,6-dimethyl-4-(3-nitrophenyl)- 3,5-pyridinedicarboxylate (34.6 g; 0.10 mmoles) and N,N-dimethylformamide dimethylacetale (14.7 g; 0.12 mmoles) in dimethylformamide is heated to reflux under nitrogen atmosphere for 16 hours.

The solvent is evaporated and the crude product is extracted with toluene and water. The organic phase is separated and, after drying over sodium sulfate, the solvent is evaporated.

Methyl 1,4-dihydro-2-(2-N,N-dimethylamino-ethyl)-6-methyl- 4-(3-nitrophenyl)-3,5-pyridinedicarboxylate is obtained which is directly hydrolyized without any further purification.

A solution of this compound (6 g; 15 mmoles) in acetone (60 ml) is treated for one hour under nitrogen atmosphere and at room temperature with hydrochloric acid 6N (6.96 ml).

The cold solution is evaporated and some water is added; the solution is filtered, the filtrate is diluted with water and extracted with methylene chloride.

After drying over sodium sulfate, the solvent is evaporated obtained methyl 1,4-dihydro-6-methyl-4-( 3-nitrophenyl)-2-(2-oxo-ethyl)-3,5-pyridinedicarboxilate, chromatographically pure oil (thin layer chromatography—eluent methylene chloride:methanol:$NH_4OH$= 94.5:5:0.5).

Mass spectrum (chemical ionization, positive ions, isobutane): m/e 374 (m+1)$^+$.

EXAMPLE 3

Preparation of methyl 1,4-dihydro-6-methyl-2-N-methyl-N-(2-(2-hydroxy-3-(2-methoxyphenoxy)propylamino)-2-methylpropyl)-aminoethyl)-4-(3-nitrophenyl)-3,5-pyridinedicarboxylate Operating in a way similar to that described in example 1 but using 1,4-dihydro-6-methyl-4-(3-nitrophenyl)- 2-(2-oxo-ethyl)-3,5-pyrinedicarboxylate as the starting aldehyde and carrying out the reduction reaction in dioxane for 12 hours methyl 1,4-dihydro-6-methyl-2-(N-methyl-N-(2-(2-hydroxy-3-(2-methoxyphenoxy)-propylamino)- 2-methylpropyl)-aminoethyl)-4-(3-nitrophenyl)- 3,5-pyridinedicarboxylate is obtained, yellow chromatographycally pure oil (thin layer chromatography— eluent methylene chloride:methanol:$NH_4OH$=94.5:5:0.5.

$^1$H-NMR (300 MHz, $CDCl_3$): delta (ppm): 1.20 (6H, 4s); 2.34 (3H, 2s); 2.44 (3H, 2s); 2.52 (2H, bd); 3.62 (6H, m); 3.83 (3H, s); 4.05 (2H, m); 4.25 (1H, m); 5.06 (1H, s); 7.35 (1H, 2t); 7.61 (1H, bd); 7.95 (1H, dd); 8.10 (1H, bs).

Working in a similar way, from the levo rotatory enantiomer of N-methyl-2-(2-hydroxy-3-(2-methoxyphenoxy)-propylamino)- 2-methylpropylamine (prepared as described in example 8) methyl 1,4-dihydro-6-methyl-(-2-(N-methyl-N-(2-(2-hydroxy- 3-(2-methoxyphenoxy)-propylamino)-2-methylpropyl)aminoethyl)- 4-(3-nitrophenyl)-3,5-pyridinedicarboxylate is obtained as a mixture of two diatereoisomers.

EXAMPLE 4

Preparation of N-methyl-3-amino-3-methyl-butyramide

A mixture of methyl 3-amino-3-methyl-butyrate hydrochloride (10.5 g; 62.6 mmoles) and methyl amine (33% solution in ethanol; 55 ml) is refluxed for 18 hours. The solvent is evaporated, the crude is dissolved in methylene chloride (100 ml) and washed with a saturate aqueous solution of sodium chloride (10 ml). After drying over sodium sulphate and evaporation of the solvent to dryness, N-methyl-3-amino-3-methyl-butyramide is obtained; chromatographically pure colorless oil (T.L.C., eluent—methylene chloride:methanol:$NH_4OH$=80:15:1)

Mass spectrum (chemical ionization, positive ions, isobutane): m/e 131 (M+1)$^+$; 114.

$^1$H-NMR (60 MHz, $CDCl_3$): delta (ppm): 1.2 (6H, s); 2.2 (2H,s); 2.8 (3H, s).

EXAMPLE 5

Preparation of (−)-N-methyl-2-(2-hydroxy-3-( 2-methoxy-phenoxy)propylamino)-2-methyl-propionamide a) A mixture of 1,2-epoxy-3-(2-methoxyphenoxy)-propane (14 g; 0.077 moles) and N-methyl-2-amino-2-methyl-propionamide (9.0 g; 0.077 moles) is absolute ethanol (90 ml) is heated at 80° C. for two hours.

After evaporation of the solvent, the crude product is dissolved in ethyl acetate (100 ml) and a solution of ethyl acetate/concentrate HCl 85:15 is added dropwise, while cooling with ice, till pH is substantially acid.

The oily phase which precipitates by acidification is separated and dissolved in water (100 ml).

The so obtained solution is brought to pH 5–6 with a dilute sodium hydroxide solution and is extracted twice with ethyl acetate (50 ml). The aqueous phase is separated and made alkaline with potassium bicarbonate; the solution is then saturated with sodium chloride and extracted with ethyl acetate (3×80 ml).

The organic phase is dried over sodium sulfate and filtered and the solvent is evaporated. N-methyl-2-(2-hydroxy-3-(2-methoxyphenoxy)-propylamino)-2-methyl-propionamide is thus obtained as a chromatographycally pure colourless oil (thin layer chromatography—eluent, chloroform:methanol:$NH_4OH$= 79:15:1).

$^1$H-NMR (300 MHz, $CDCl_3$): delta (ppm): 1.35 (6H, s); 1.70 (2H, bs; exchange with $D_2O$); 2.72 (2H, m); 2.78 (3H, d); 3.85 (3H, s); 3.98 (1H, dd); 4.05 (1H, m); 4.15 (1H, dd); 6.90–7.02 (4H, m); 7.35 (1H, bq).

Mass spectrum (chemical ionization, positive ions, isobutane): m/e 297 (M+1)$^+$; 238.

b) A mixture of N-methyl-2-(2-hydroxy-3-( 2-methoxyphenoxy)propylamino)-2-methyl-propionamide (146 g; 0.49 moles) and (+)-camphosulfonic acid (114 g; 0.49 moles) in ethyl acetate (1.5 l) is heated to reflux until completely dissolved.

The solution is cooled to room temperature and after 10 hours is filtered.

The crystalline product which separates is washed with little ethyl acetate and recrystallized three times from isopropyl alcohol to obtain (−)-N-methyl-2-(2-hydroxy-3-(2-methoxyphenoxy)-propylamino)-2-methyl-propionamide camphosulfonate as a crystalline white solid melting at 154°–156° C., (alpha)$_D$=+12.25° (c=5% , ethanol).

A solution of this salt is made alkaline with potassium carbonate and extracted with methylene chloride to give the corresponding free base in the form of a colourless oil.

Operating in a similar way, the following compounds were prepared:

N-isopropyl-2-(2-hydroxy-3-(2-methoxyphenoxy)-propylamino)- 2-methylpropionamide Mass spectrum (chemical ionization, positive ions, isobutane): m/e 325 (M+1)$^+$;238

$^1$H-NMR (300 MHz, CDCl$_3$): delta (ppm): 1.38 (6H, d); 1.58 (6H, s); 2.96 (2H, m); 4.12 (3H, s); 4.21–4.38 (4H); 7.14–7.28 (4H).

N-butyl-2-(2-hydroxy-3-(2-methoxyphenoxy)-propylamino)- 2-methyl-propionamide

Mass spectrum (chemical ionization, positive ions, isobutane): m/e 339 (M+1)$^{30}$; 238.

$^1$H-NMR (300 MHz, CDCl$_3$): (ppm): 1.15 (3H, t); 1.58 (6H, s); 1.48–1.75 (4H); 2.96 (2H, m); 3.45 (2H); q); 4.11 (3H, s); 4.20–4.63 (3H;) 7.13–7.28 (4H).

2-(2-hydroxy-3-(2-methoxyphenoxy)-propylamino)-2-methyl-propionamide

Mass spectrum (chemical ionization, positive ions, isobutane): m/e 283 (M+1)$^+$; 238.

$^1$H-NMR (300 MHz, CDCl$_3$): delta (ppm): 1.35 (6H, s); 2.78 (2H, m); 3.85 (3H, s); 3.98 (1H, dd); 4.05 (1H, m); 4.10 (1H, dd); 6.88–7.02 (4H, m).

N-methyl-3-(2-hydroxy-3-(2-methoxyphenoxy)-propylamino- 3-methyl-butyramide

Mass spectrum (chemical ionization, positive ions, NH$_4$OH): m/e 311 (M+1)$^+$; 143.

$^1$H-NMR (300 MHz), CDCl$_3$: delta (ppm): 1.14 and 1.15 (6H, 2s); 2.26 (2H, s); 2.73 (3H, d), 2.75 (2H, m), 3.75 (3H, s); 370–4.10 (3H); 6.86–7.03 (4H).

N-methyl-2-(2-hydroxy-3-(1-naphthoxy)-propylamino)-2-methyl-propionamide

Mass spectrum (chemical ionization, positive ions, NH$_4$OH) m/e 317 (M+1)$^+$;258.

$^1$H-NMR (300 Mhz, CDCl$_3$): delta (ppm); 1.32 and 1.33 (6H, 2s); 2.65 (3H, d); 2.78 (1H, dd), 2.86 (1H, dd); 4.15–4.24 (3H); 6.80 (1H) d); 7.36 (1H, t); 7.42–7.52 (3H); 7.80 (1H, bd); 8.20 (1H, bd).

N-methyl-2-(2-hydroxy-3-(4-carbazolyloxy)-propylamino)- 2-methyl-propionamide

Mass spectrum (chemical ionization, positive ions, NH$_4$HO) m/e 356 (M+1)$^+$; 297.

$^1$H-NMR (300 MHz, CDCl$_3$): delta (ppm): 1.35 (6H, s); 2.68 and 2.70 (3H, 2s); 2.78–2.94 (2H); 4.20–4.30 (3H); 6.67 (1H, d); 7.08 (1H, d); 7.18–7.44 (4H); 8.21 (1H, d)

The above mentioned compounds have been obtained in the form of chromatographically pure oils (T.L.C.; eluent, methylene chloride:methanol:NH$_4$OH=94.5:5:0.5)

EXAMPLE 6

Preparation of (–)-N-methyl-2-((2-hydroxy-3-(2-methoxyphenoxy)-propyl)-triphenylmethylamino)-2-methylpropionamide A mixture of (–)-N-methyl-2-(2-hydroxy-3-( 2-methoxyphenoxy)-propylamino)-2-methyl-propionanide (18.0 g; 0.061 moles), prepared as disclosed in example 4, triphenylmethyl chloride (17.5 g; 0.061 moles) and triethylamine (12 ml; 0.085 moles) in toluene (180 ml) is refluxed under stirring for 10 hours. After cooling to room temperature, the reaction mixture is washed with water (100 ml), with a potassium bicarbonate aqueous solution (80 ml) and finally with water (80 ml) again.

The organic phase is dried over sodium sulfate and filtered. The solid crude product obtained after evaporation of the solvent, is purified by chromatography on silica gel column (230–400 mesh) eluting with methylene chloride. (–)-N-methyl-2-((2-hydroxy-3-( 2-methoxyphenoxy)-propyl)-triphenylmethylamino)-2-methylpropionamide is obtained as a chromatographycally pure oil (thin layer chromatography— eluent, ethyl acetate:gasoline=8:2). (alpha)$_D$=–40.2° (c=5%, ethanol).

$^1$H-NMR (300 MHz, CDCl$_3$): delta (ppm); 1.14 (3H, s); 1.22 (3H, s); 2.33 (1H, dd); 2.48 (3H, d); 2.68 (1H, dd); 3.55 (1H, dd); 3.76 (3H, s); 4.00–4.10 (2H; 6.62 (1H, bd); 6.80–6.95 (3H, m); 7.20–7.35 (9H, m); 7.50 (6H, bd).

Operating in a similar way, the following compounds were prepared:

N-isopropyl-2-((2-hydroxy-3-(2-methoxyphenoxy)-propyl)-triphenylmethylamino)-2-methylpropionamide Chromatographically pure oil (thin layer chromatography— eluent, methylene chloride:methanol:NH$_4$OH= 98:4:0.2

Mass spectrum (chemical ionization, positive ions, ammonium hydroxide); m/e 568 (M+2)$^{30}$; 325; 243.

$^1$H-NMR (300 MHz, CDCl$_3$): delta (ppm): 0.89 (3H, d); 0.92 (3H, d); 1.10 (3H, s); 1.21 (3H, s); 2.42 (1H, dd); 2.57 (1H, dd); 3.64 (1H, dd); 3.75 (3H, s); 3.87 (1H, m); 3.99 (1H, dd); 4.03 (1H, m); 6.63 (1H, bd); 6.80–6.94 (3H); 7.20–7.32 (9H, m); 7.52 (6H, bd).

N-butyl-2-((2-hydroxy-3-(2-methoxyphenoxy)-propyl)-triphenyl-methylamino)-2-methylpropionamide chromatographically pure oil (thin layer chromatography— eluent, methylene chloride:methanol:NH$_4$OH= 160:15/1)

Mass spectrum (chemical ionization, positive ions, ammonium hydroxide): m/e 581 (M+1)$^+$; 339; 243.

$^1$-HMR (300 MHz, CDCl$_3$): delta (ppm): 0.78 (3H, t); 1.12 (3H, s); 1.22 (3H, s); 1.08–1.25 (4H); 2.37 (1H, dd); 2.58 (1H, dd); 2.85 (1H, m); 3.05 (1H, m); 3.59 (1H, dd); 3.76 (3H, s); 4.01 (1H, dd); 4.01 (1H, m); 6.63 (1H, bd); 6.80–6.95 (3H); 7.20–7.35 (9H, m); 7.50 (6H, bd).

2-((2-hydroxy-3-(2-methoxyphenoxy) propyltriphenylmethylamino)-2-methylpropionamide Chromatographicaaly pure oil (thin layer chromatography— eluent, methylene chloride:methanol:NH$_4$OH=

160:15:1)

Mass spectrum (chemical ionization, positive ions, ammonium hydroxide): m/e 525 (M+1)$^+$; 480; 243; 115.

$^1$H-NMR (300 Mhz, CDCl$_3$): delta (ppm); 1.16 (3H, s); 1.25 (3H, s); 2.41 (1H, dd); 2.60 (1H, dd); 3.61 (1H, dd); 4.01 (1H, dd); 4.04 (1H, m); 6.58 (1H, bd); 6.80–6.94 (3H, m); 7.22–7.35 (9H, m); 7.50 (6H, bd).

EXAMPLE 7

Preparation of (–)-N-(2-(2-hydroxy-3-(2-methoxyphenoxy)propyl)-triphenylmethylamino)-2-methoxypropyl)-methylamine A solution of (–)-N-methyl-2-((2-hydroxy-3-( 2-methoxyphenoxy)-proyl)-triphenylmethylamino)-2-methylpropionamide (25.1 g; 0.047 moles), prepared as described in example 6, in tetrahydrofuran (200 ml) is added, dropwise under stirring and in a inert atmosphere, to a suspension of lithium aluminium hydride (3.55 g; 0.093 moles) in anhydrous tetrahydrofuran (50 ml).

On completion of the addition, the reaction mixture is heated to reflux for two hours.

After cooling on a ice bath, the lithium aluminum hydride excess is decomposed by adding in succession dropwise a solution of tetrahydrofuran/water 9:1 (5 ml), and then water (4 ml), 15% sodium hydroxide (4 ml), and again water (10 ml).

The precipitate is filtered and washed with ethyl ether; the organic phase is dried over sodium sulfate and filtered. (–)-N-(2-((2-hydroxy-3-( 2-methoxyphenoxy)-propyl)-triphenylmethylamino)- 2-methylpropyl)-methylamine is obtained by solvent evaporation.

Mass spectrum (chemical ionization, positive ions, ammonium hydroxide): m/e 526 (M+2)$^+$; 243.

$^1$H-NMR (300 MHz, CDCl$_3$): delta (ppm): 0.92 (3H, s); 1.00 (3H, s); 2.30 (3H, s); 2.34 (2H, s); 2.35–2.46 (2H, m); 3.68 (1H, dd); 3.80 (3H, s); 4.01 (1H, dd); 4.05 (1H, m); 6.68 (1H, bd); 6.80–6.90 (3H, m); 7.20–7.34 (9H, m); 7.52 (6H, bd).

Working in a similar way the following compounds were prepared:

N-(2-((2-hydroxy-3-(2-methoxyphenoxy)-propyltriphenylmethylamino)-2-methylpropyl)-isopropylamine chromatographycally pure oil (thin layer chromatography— eluent, CH$_2$Cl$_2$:methanol:NH$_4$OH=98:4:0.2)

Mass spectrum (chemical ionization, positive ions, ammonium hydroxide): m/e 554 (M+2)$^+$; 243.

$^1$H-NMR (300 MHz, CDCl$_3$): delta (ppm); 0.88–0.95 (12H); 2.32 (2H, s); 2.45 (2H, bd); 2.60 (1H; m); 3.62 (1H, ddd); 3.79 (3H, s); 3.94 (1H, dd); 3.98 (1H, m); 6.64 (1H, d); 6.83 (3H, m), 7.25 (9H, m); 7.52 (6H, bd).

N-(2-((2-hydroxy-3-( 2-methoxyphenoxy)-propyltriphenylmethylamino)-2-methylpropyl)-butylamine chromatographycally pure oil (thin layer chromatography— eluent, CH$_2$Cl$_2$:methanol:NH$_4$OH=98:4:0.2

Mass spectrum (chemical ionization, positive ion, ammonium hydroxide): m/e 568 (M+2)$^+$; 243

$^1$H-NMR (300 MHz, CDCl$_3$); delta (ppm): 0.83 (3H, t); 0.92 (3H, s); 0.98 (3H, s); 1.20 (2H, m); 1.33 (2H, m); 2.37 (2H, s); 2.40–2.52 (4H); 3.65 (1H, dd); 3.80 (3H, s); 3.96 (1H, dd); 3.99 (1H, m); 6.65 (1H, bd); 6.74 (3H, m); 7.26 (9H, m); 7.52 (6H, bd).

2-((2-hydroxy-3-(2-methoxyphenoxy)-propyltriphenylmethylamino)-2-methylpropyl)-methylpropylamine chromatographycally pure oil (thin layer chromatography— eluent, CH$_2$Cl$_2$:methanol:NH$_4$OH=160:15:1)

Mass spectrum (chemical ionization, positive ions, ammonium hydroxide): m/e 512 (M+2)$^+$; 480; 243.

$^1$H-NMR (300 MHz, CDCl$_3$): delta (ppm); 0.85 (3H, s); 0.89 (3H, s); 2.38 (2H, s); 2.42 (2H, d); 3.70 (1H, dd); 3.80 (3H, s); 4.00 (2H, m), 6.65 (1H, dd); 6.80–6.90 (3H, m); 7.20–7.30 (9H, m); 7.50–7.55 (6H, m).

EXAMPLE 8

Preparation of (–) N-methyl-2-(2-hydroxy-3-(2-methoxyphenoxy)propylamino)-2-methylpropylamine oxalate A solution of (–) N-methyl-2-(2-hydroxy-3-( 2-methoxyphenoxy)-propylamino)-2-methylpropyionamide (50 g; 0.017 moles), prepared as described in example 4b, and borane methyl sulfite (78.2 ml; 0.82 moles) in tetrahydrofuran (500 ml) is maintained under reflux for 3 hours under nitrogen atmosphere.

The reaction mixture is cooled to 5° C. and a solution of concentrate HCl (35 ml) in methanol (200 ml) is slowly added; the mixture is then refluxed for 1 hour. The solvent is evaporated and the crude is collected with water (100 ml). The mixture is made alkaline to pH 8 with dilute ammonia. After addition of potassium bicarbonate till saturation, the mixture is extracted with methylene chloride. The organic phase is dried over sodium sulphate, filtered and evaporated to dryness. The residue is dissolved in hot ethyl acetate (300 ml). The mixture is cooled and a solution of oxalic acid in ethyl acetate is added till acid pH.

After half an hour at room temperature, the crystalline solid is separated by filtration, washed with ethyl acetate and then with ethyl ether. After drying, (–) N-methyl-2-(2-hydroxy- 3-(2-methoxyphenoxy)-methylpropylamino)-2-propylamine oxalate is obtained in the form of a whithe solid melting at 150°–152° C.

The base shows an (alpha)$_D$=–10.8 (water, c=0.5%)

Working in a similar way the following compounds were prepared:

N-methyl-3-(2-hydroxy-3-(2-methoxyphenoxy)-propylamino)- 3-methylbutylamine

White solid, m.p. 93° C.

Mass spectrum (chemical ionization, positive ions, ammonium hydroxide; m/e 297 (M+1)$^+$;

$^1$H-NMR (300 MHz, CDCl$_3$): delta (ppm): 1.11 (6H, s); 1.62 (2H, bt); 2.42 (3H, s); 2.70 (2H, bt); 2.73 (1H, dd), 2.86 (1H, dd); 3.83 (3H, s); 4.01 (1H, m); 4.2 (2H, bs), 6.84–6.95 (4H).

N-methyl-2-(2-hydroxy-3-(1naphthoxy)-propylamino)-2-methylpropylamine

Chromatographically pure oil (T.L.C.; eluent, methylene chloride:methanol:ammonium hydroxide=86:10:0.6)

Mass spectrum (chemical ionization, positive ions, ammonium hydroxide): m/e 303 (M+1)⁺; 258

¹H-NMR (300 MHz, CDCl$_3$): delta(ppm); 1.07 and 1.08 (6H, 2s); 2.41 (3H, s); 2.47 (2H, d); 2.75 (1H, dd); 2.92 (1H, dd); 4.08–4.21 (3H); 6.82 (1H, d); 7.32–7.50 (4H); 7.79 (1H, m). 8.25 (1H, m).

N-methyl-2-(2-hydroxy-3-(4-carbazolyloxy)-propylamino)-2-methylpropylamine

Chromatographically pure oil (T.L.C.; eluent, methylene chloride:methanol:NH$_4$OH=86:10:0.6)

Mass spectrum (chemical ionization, positive ions, ammonium hydroxide): m/e 342 (M+1)⁺;29

¹H-NMR (300 Mhz, CDCl$_3$) delta (ppm): 1.09 and 1.11 (6H, 2s); 2.42 (3H, s); 2.50 (2H, d); 2.85 (1H, dd); 3.00 (1H, dd); 4.12–4.30 (3H); 6.66 (1H, d); 7.02 (1H, d); 7.18–7.40 (3H); 8.29 (1H, d)

EXAMPLE 9

Preparation of ethyl 1,4-dihydro-6-methyl-2-(N-methyl-N-(2-((2-hydroxy-3-(2-methoxyphenoxy)-propyl)-triphenylmethylamino)-2-methylpropyl)-aminomethyl-4-(3-nitrophenyl)-3,5-pyridinedicarboxylate A mixture of (–)-N-(2-(2-hydroxy-3-( 2-methoxyphenoxy)-propyl)-triphenylmethylamino)-2-methylpropyl)-methylamine (23.4 g; 0.045 moles) prepared as disclosed in example 7, 2-bromoethyl- 1,4-dihydro-6-methyl-4-(3-nitrophenyl)-3,5-pyridinedicarboxylate (20.2 g; 0.045 moles) and triethylamine (9.2 ml; 0.066 moles) in toluene (230 ml) is stirred at room temperature for three hours.

The reaction mixture is washed with water (200 ml), with a saturate potassium bicarbonate solution (150 ml) and again with water (100 ml).

After drying over sodium sulfate the organic phase is filtered and the solvent evaporated.

The reaction crude product is purified by chromatography on silica gel column (230–400 mesh), eluent—petroleum ether; ethyl acetate:ethanol:propylamine=100:100:0.5:1. Ethyl 1,4-dihydro-6-methyl-2-(N-methyl-N-(2(( 2-hydroxy-3-(2-methoxyphenoxy)-propyl)-triphenylmethylamino)-2-methylpropyl)-aminomethyl)- 4-(3-nitrophenyl)-3,5-pyridinedicarboxylate is obtained.

The chromatographic analysis (thin layer chromatography— eluent, CH$_2$Cl$_2$:methanol:NH$_4$OH=98.2:2:0.2) shows two spots corresponding to the two enantiomers of the two diastereomeric pairs.

Mass spectrum (chemical ionization, negative ions, isobutane): m/e 654 (M-CPh$_3$)⁻; 623;415;123.

¹H-NMR (300 MHz, CDCl$_3$) delta (ppm): 0.90–1.40 (6H, 4s); 1.16–1.26 (6H, m); 2.20 (3H, 2s) 2.28 (3H, s); 2.24–2.40 (2H, m); 2.50–2.70 (2H, m); 3.75 (3H, s); 3.84–4.15 (7H); 5.01 and 5.50 (1H, 2s); 6.30 (1H, bd); 6.70–6.90 (3H, m); 7.20–7.32 (9H, m); 7.47–7.52 (7H); 7.59 (1H, bd); 7.96 (1H, m); 8.11 (1H, bs).

Working in a similar way, the following compounds were prepared:

ethyl 1,4-dihydro-6-methyl-2-(N-isopropyl-N-(2-((2-hydroxy-3(2-methoxyphenoxy)-propyl)-triphenylmethylamino)-2-methylpropyl)-aminomethyl)-4-(3-nitrophenyl)-3,5-pyridinedicarboxylate (thin layer chromatography—eluent, CH$_2$Cl$_2$:methanol:NH$_4$OH=98:2:0.2, two spots corresponding to the two racemic diastereoisomers)

¹H-NMR (300 MHz, CDCl$_3$): delta (ppm): 0.90–1.30 (18H); 2.15–2.40 (5H); 2.60–2.80 (2H, m); 3.50 (1H, dd); 3.70 (2H, bd); 3.74 (3H, s); 5.01 and 5.05 (1H, 2s); 6.50 (1H, bd); 6.80 (3H, m); 7.28 (9H, m), 7.44–7.52 (7H); 7.60 (1H, m); 7.95 (1H, bd); 8.12 (1H, bd).

ethyl 1,4-dihydro-6-methyl-2-(N-butyl-N-(2-((2-hydroxy-3-(2-methoxyphenoxy)-propyl)-triphenylmethylamino)-2-methylpropyl)aminomethyl)-4-(3-nitrophenyl)-3,5-pyridinedicarboxylate (thin layer chromatography—eluent, CH$_2$Cl$_2$:methanol:NH$_4$OH=98:2:0.2)

Mass spectrum (chemical ionization, negative ions, isobutane): m/e 936 (M+1)⁻; 694; 664; 457; 444.

¹H-NMR (300 MHz, CDCl$_3$): delta (ppm): 0.82 and 0.84 (3H, 2t); 0.92–1.04 (6H, 4s); 1.16 (2H, m); 1.22 (6H, m); 1.34 (2H, m); 2.18 and 2.21 (3H, 2s; 2.30–2.46 (4H); 2.60 (2H, m); 3.59 (2H, m); 3.75 (3H, s), 3.80–4.12 (7H); 5.01 and 5.05 (1H, 2s); 6.52 (1H, bd); 6.80 (3H, m), 7.25 (9H, m); 7.50 (7H); 7.57 (1H, bd); 7.95 (1H, bd); 8.10 (1H, bs).

ethyl, 1,4-dihydro-6-methyl-2-(N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate (thin layer chromatography—eluent, CH$_2$Cl$_2$:methanol:NH$_4$OH=98:2:0.2)

Mass spectrum (chemical ionization, negative ions, isobutane): m/e 882 (M)⁻; 640; 402; 243;123.

¹H-NMR (300 MHz, CDCl$_3$): delta (ppm): 0.93–1.10 (6H); 1.16–1.25 (6H, 2t); 2.15–2.54 (7H); 3.62–3.83 (3H, m); 3.80 (3H, s); 3.98–4.10 (6H, m); 5.08 (1H, bd); 6.64 (1H, bd); 6.76–6.90 (3H, m); 7.20–7.48 (10H); 7.52 (6H, bd); 7.59 (1H, bd); 7.98 (1H, bd); 8.09 (1H, bs); 8.44 (1H, bs).

EXAMPLE 10

Preparation of ethyl (–)-1,4-dihydro-6-methyl-2-(N-methyl-N-(2-(2-hydroxy-3-(2-methoxyphenoxy)-propylamino)-2-methylpropyl)-aminomethyl)-4-(3-nitrophenyl)-3,5-pyridinedicarboxylate Concentrate hydrochloric acid (7 ml) is added to a solution of ethyl 1,4-dihydro-6-methyl-2-(N-methyl-N-( 2-((2-hydroxy-3-( 2-methoxyphenoxy)-propyl)-triphenylmethylamino)-2-methylpropyl)-aminomethyl)- 4-(3-nitrophenyl)-3,5-pyridinedicarboxylate (3.4 g; 3.9 mmoles, prepared as described in example 9, in tetrahydrofuran (40 ml). After one hour at room temperature the solvent is evaporated in vacuum at 40° C.

The crude product is dissolved in methylene chloride (60 ml), washed with an aqueous potassium bicarbonate solution (40 ml) and with water (40 ml).

After drying over soodium sulfate, the organic phase is filtered and the solvent is evaporated.

The crude product is chromatoographed on a silica gel column (230–400 mesh) eluting with petroleum ether:ethyl acetate:ethanol:triethylamine= 10:10:0.2:0.5.

The two levorotatory enantiomers of the two racemic pairs of distereomeric ethyl 1,4-dihydro-6-methyl-2-(N-methyl-N-( 2-(2-hydroxy-3-(2-methoxphenyl)-propylamino)-2-methoxylpropyl)aminomethyl)-4-(3-nitrophenyl)- 3,5-pyridinedicarbooxylate are thus separated and then converted in their dihydrochloride salts by dissolution in ethyl ether and treatment with an anhydrous saturate solution of HCl in ethyl ether.

Diastereoisomer A (greater Rf) (dihydrochloride), crystalline yellow solid; m.p.=138°–141° C.; (alpha)$_D$=15.3° (c=5%, dimethylsulfoxyde).

Diatereoisomer B (lower Rf) (dihydrochloride), amorphous yellow solid; m.p.=110°–115° C.; (alpha)$_D$=+5.7 (c=5%, dimethylsulfoxyde).

Mass spectrum (chemical ionization, positive ions, isobutane): m/e 655 (M+1)$^+$; 625; 531; 238.

Diatereoisomer A:

$^1$H-NMR (free base) (300 MHz, CDCL$_3$): delta (ppm): 1.12 (3H, s); 1.14 (3H, s); 1.20 (3H, t); 1.22 (3H, t); 2.38 and 2.39 (6H, 2s); 2.54 (2H, d); 2.70–2.85 (2H, m); 3.84 (3H, s); 3.91 (2H, s); 3.96–4.14 (7H); 5.06 (1H, s); 6.85–6.98 (4H); 7.35 (1H, t); 7.62 (1H, bd); 7.97 (1H, bd); 8.12 (1H, t).

Diatereoisomer B:

$^1$H-NMR (free base) (300 MHz, CDCl$_3$): delta (ppm): 1.12 (3H, s); 1.14 (3H, s); 1.20 (3H, t); 1.22 (3H, t) 2.38 and 2.39 (6H, 2s); 2.54 (2H, d); 2.70–2.85 (2H, m); 3.84 (3H,s); 3.91 (2H, s); 3.96–4.14 (7H); 5.06 (1H, s); 6.85–6.98 (4H); 7.34 (1H, t); 7.62 (1H, bd); 7.97 (1H, bd); 8.12 (1H, t).

Working in a similar way, the following compounds were prepared:

ethyl 1,4-dihydro-6-methyl-2-(N-isopropyl-N-(2-(2-hydroxy-3-(2-methoxyphenoxy)-propylamino)-2-methylpropyl)- aminomethyl)-4-(3-nitrophenyl)-3,5-pyridinedicarboxylate Diastereoisomer C (greater Rf) (dihydrochloride), amorphous yellow solid; m.p.=117°–120° C.

Diastereoisomer D (lower Rf) (dihydrochloride), amorphous yellow solid; m.p.=119°–122° C.

Mass spectrum (chemical ionization, positive ions, isobutane): m/e 683 (M+1)$^+$; 653; 560; 444; 432; 238; 201; 125.

$^1$H-NMR (free base) (300 MHz, CDCl$_3$): delta (ppm)

Diastereoisomer C: 113 and 1.15 (6H, 2d); 1.11 and 1.12 (6H, 2s); 1.21 and 1.22 (6H, 2t); 2.40 (3H, s); 2.50 (2H, bs); 2.73–2.90 (5H); 3.84 (3H, s); 3.95–4.15 (7H); 5.09 (1H, s) 6.90 (4H, m); 7.33 (1H, t); 7.61 (1H, bd); 7.96 (1H, bd); 8.10 (1H, bs).

Diastereoisomer D: 1.13 and 1.15 (6H, 2d); 1.11 and 1.13 (6H, 2s); 1.21 and 1.22 (6H, 2t); 2.39 (3H, s); 2.51 (2H, dd); 2.73–2.90 (5H); 3.84 (3H, s); 3.95–4.15 (7H); 5.09 (1H, s) 6.90 (4H, m); 7.33 (1H, t); 7.61 (1H, bd); 7.96 (1H, bd); 8.10 (1H, bs).

ethyl 1,4-dihydro-6-methyl-2-(N-butyl-N-(2-(2-hydroxy-3-(2-methoxyphenoxy)-propylamino)-2-methylpropyl)-aminomethyl)-4-(3-nitrophenyl)-3,5-pyridinedicarboxylate Diastereoisomer E (greater Rf) (dihydrochloride), crystalline yellow solid; m.p.=108°–110° C.

Diastereoisomer F (lower Rf) (dihydrochloride), amorphous yellow solid; m.p.=113°–120° C.

Mass spectrum (chemical ionization, positive ions, isobutane): m/e 697 (M+1)$^+$; 458;446;257;201;125.

$^1$H-NMR (free base) (300 MHz, CDCl$_3$): delta (ppm)

Diastereoisomer E: 0.90 (3H, t); 1.10 and 1.11 (6H, 2s; 1.21 and 1.22 (6H, 2t); 1.30 (2H, m); 1.43 (2H, m); 2.39 (3H, s); 2.50–2.75 (8H); 3.84 (3H, s); 3.90–4.15 (7H); 5.08 (1H, s); 6.90 (4H, m); 7.33 (1H, t); 7.61 (1H, bd); 7.96 (1H, bd); 8.11 (1H, bs).

Diastereoisomer F: 0.90 (3H, t); 1.10 and 1.12 (6H, 2s); 1.21 and 1.22 (6H, 2t); 1.30 (2H, m); 1.43 (2H, m); 2.38 (3H, s); 2.50–2.75 (8H); 3.84 (3H, s); 3.90–4.15 (7H); 5.08 (1H, s); 6.90 (4H, m); 7.33 (1H, t); 7.61 (1H, bd); 7.96 (1H, bd); 8.11 (1H, bs).

EXAMPLE 11

Preparation of ethyl 1,4-dihydro-6-methyl-2-(N-ethyl-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate A mixture of ethyl 1,4-dihydro-6-methyl-2-(N-(2-(2-hydroxy-3-(2-methoxyphenoxy)-propyl)-triphenylmethylamino)-2-methylpropyl)-aminomethyl)-4-(3-nitrophenyl)-3,5-pyridinedicarboxylate (20.6 g; 23.4 mmoles), prepared as disclosed in example 9, diethylsulfate (3.3 ml; 25.3 mmoles), triethylamine (5 ml; 34.6 mmoles) and tetrabutylammonium hydrogen sulfate (2.4 g; 7.0 mmoles) in toluene (200 ml) is heated to reflux for 5 hours.

After evaporation of the solvent, the crude product is extracted with methylene chloride (200 ml) and water (100 ml).

The organic phase is separated, dried over sodium sulfate and filtered. By solvent evaporation a crude product is obtained, which is purified by chromatography on silica gel column (230–400 mesh), eluting with petroleum ether:ethyl acetate:propylamine=120:89:0.3.

Chromatographically pure ethyl 1,4-dihydro-6-methyl-2-(N-ethyl-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate is thus obtained.

$^1$H-NMR (300 MHz, CDCl$_3$): delta (ppm) 0.9–1.5 (9H); 1.18–1.25 (6H, m); 2.18 and 2.22 (3H, 2s); 2.25–2.74 (6H, m); 3.75 (3H, s); 3.78–4.10 (9H, m); 5.01 and 5.06 (1H, 2s); 6.51 (1H, bd); 6.65–6.88 (3H, m); 7.18–7.31 (9H, m); 7.45–7.53 (7H, m); 7.58 (1H, bd); 7.95 (1H, bd); 8.10 (1H, bs); 9.02 and 9.12 (1H, bs).

Mass spectrum (chemical ionization, positive ions, isobutane): m/e 910 (M)$^+$; 699; 417.

Working in a similar way but using allyl iodide and benzyl bromide, respectively, as alkylating agents the following compounds were prepared.

Ethyl 1,4-dihydro-6-methyl-2-(N-2-propenyl-N-(2-(2-hydroxy-3-(2-methoxyphenoxy)-propyl)-triphenylmethylamino)-2-methylpropyl)-aminomethyl)-4-(3-nitrophenyl)-3,5-pyridinedicarboxylate $^1$H-NMR (300 MHz, CDCl$_3$): delta (ppm): 0.90–1.05 (6H, 4s); 1.16–1.20 (6H, m); 2.18 and 2.24 (3H, 2s); 2.39 (2H, dd); 2.50–2.75 (2H, m); 3.00–3.20 (2H, m); 3.50–4.15 (9H); 3.74 (3H, s); 4.90–5.80 (3H, m); 5.70–5.80 (1H, m); 6.50 (1H, dd); 6.70–6.88 (3H, m); 7.20–7.32 (9H, m);

7.45–7.60 (8H, m); 7.95 (1H, bd); 8.10 (1H, bs).

ethyl
1,4-dihydro-6-methyl-2-(N-benzyl-N-(2-(2-hydroxy-3-
(2-methoxyphenoxy)-propyl)-
triphenylmethylamino)-2-methylpropyl)-
aminomethyl)-4-
(3-nitrophenyl)-3,5-pyridinedicarboxylate $^1$H-NMR (300 MHz, CDCl$_3$): delta (ppm) 0.85–0.95 (6H, m); 2.20 and 2.28 (3H, 2s); 2.30–2.78 (4H); 3.72 and 3.74 (3H, 2s); 3.50–4.10 (11H); 4.98 (1H, bs); 6.46 (1H, m); 6.65–6.86 (3H, m); 7.10–7.30 (16H, m); 7.45–7.54 (6H, m); 7.92 (1H, bd); 8.10 (1H, bd).

EXAMPLE 12

Preparation of ethyl
1,4-dihydro-6-methyl-2-(N-ethyl-N-(2-(2-hydroxy-
3-(2-methoxyphenoxy)-propylamino)-2-methylpropyl)-
aminomethyl)-4-(3-nitrophenyl)-3,5-
pyridinedicarboxylate Concentrate hydrochloric acid (7.1 ml) is added to a solution of ethyl 1,4-dihydro-6-methyl-2-(N-ethyl-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate (3.5 g; 3.9 mmoles), prepared as disclosed in example 11, in tetrahydrofuran (40 ml). After one hour at room temperature the solvent is evaporated in vacuum at 40° C. The crude solid is dissolved in methylene chloride (60 ml), washed with a potassium bicarbonate saturate aqueous solution (40 ml) and the organic phase is dried over sodium sulfate and filtered.

After evaporation of the solvent, the crude product is purified by chromatography on silica gel column (230–400 mesh) eluting with petroleum ether:ethyl acetate;triethyl amine:ethanol=10:10:0.5:0.2.

The two ethyl 1,4-dihydro-6-methyl-2-(N-ethyl-N-(2-(2-hydroxy-3-(2-methoxyphenoxy)-propylamino)-2-methylpropyl)-amino methyl)-4-(3-nitrophenyl)-3,5-pyridinedicarboxylate diastereoisomers are thus separated and then converted in their dihydrochloride salts by treatment with a solution of hydrochloric acid in ethyl ether.

Diastereoisomer G: (greater Rf) (dihydrochloride), amorphous yellow, solid; m.p.=116°–118° C.

Diastereoisomer H: (lower Rf) (dihydrochloride), amorphous yellow solid; m.p.=117°–120° C.

Mass spectrum (chemical ionization, positive ions, isobutane): m/e 670 (M+2)$^+$; 238.

$^1$H-NMR (free base) (300 MHz, CDCl$_3$): delta (ppm)

Diastereoisomer G: 1.10 and 1.11 (6H, 2s); 1.20 (3H, t); 1.22 (3H, t); 2.40 (3H, s); 2.55 (2H, bs); 2.62 (2H, q); 2.75–2.88 (2H, m); 3.84 (3H, s); 3.90–4.15 (7H); 5.08 (1H, s); 6.86–6.98 (4H, m); 7.33 (1H, t); 7.51 (1H, bd); 7.96 (1H, bd); 8.10 (1H, bs).

Diastereoisomer H: 1.10 and 1.12 (6H, 2s); 1.20 (3H, t); 1.22 (3H, t); 2.40 (3H, s); 2.55 (2H, bs); 2.62 (2H, q); 2.75–2.88 (2H, m); 3.84 (3H, s); 3.90–4.15 (7H); 5.078 (1H, s); 6.86–6.98 (4H, m); 7.33 (1H, t); 7.51 (1H, bd); 7.96 (1H, bd); 8.10 (1H, bs).

Working in a similar way, the following compounds were prepared:

ethyl 1,4-dihydro-6-methyl-2-(N-2-propenyl-N-(2-2-hydroxy-3-( 2-methoxyphenoxy)-
propylamino)-2-methylpropyl)-aminomethyl)-4-
(3-nitrophenyl)-3,5-pyridinedicarboxylate Diastereoisomer I: (greater Rf)

Diastereoisomer J: (lower Rf)

Both the diastereoisomers I and J (dihydrochloride) melt at 90°–95° C.

Mass spectrum (chemical ionization, positive ions, ammonium hydroxide): m/e 681 (M+1)$^+$; 238.

$^1$H-NMR (free base) (300 MHz, CDCl$_3$): delta (ppm)

Diastereoisomer I: 1.10 and 1.11 (6H, 2s); 1.20 and 1.22 (6H, 2t); 2.40 (3H, s); 2.57 (2H, bs); 2.76 (2H, m); 3.18 (2H, d); 3.85 (3H, s); 3.90–4.15 (9H); 5.08 (1H, s); 5.12 (1H, m); 5.18 (1H, bs); 5.85 (1H, m); 6.84–6.98 (4H); 7.34 (1H, t); 7.11 (1H, bd); 7.97 (1H, dd); 8.11 (1H, bs).

Diastereoisomer J: 1.10 and 1.12 (6H, 2s); 1.20 and 1.22 (6H, 2t); 2.40 (3H, s); 2.57 (2H, bs); 2.76 (2H, m); 3.18 (2H, 2d); 3.85 (3H, s); 3.90–4.15 (9H); 5.08 (1H, s); 5.12 (1H, m); 5.18 (1H, bs); 5.85 (1H, m); 6.84–6.98 (4H); 7.34 (1H, t); 7.11 (1H, bd); 7.97 (1H, dd); 8.11 (1H, bs).

Ethyl
1,4-dihydro-6-methyl-2-(N-benzyl-N-(2-(2-hydroxy-3-
(2-methoxyphenoxy)-propylamino)-2-methylpropyl)-
aminomethyl)-
4-(3-nitrophenyl)-3,5-pyridinedicarboxylate Diastereoisomer K: (greater Rf)

Diastereoisomer L: (lower Rf)

Both the diastereoisomers K and L (dihydrochloride) melt at 90°–95° C.

Mass spectrum (chemical ionization, positive ions, ammonium hydroxide): m/e 731 (M+1)$^+$; 238

$^1$H-NMR (free base) (300 MHz, CDCl$_3$): delta (ppm):

Diastereoisomer K: 1.04 and 1.05 (6H, 2s); 1.18 and 1.20 (6H, 2t); 2.38 (3H, s); 2.71 (2H, d); 2.79 (2H, d); 3.72 (2H, dd); 3.83 (3H, s); 3.90–4.24 (9H); 5.01 (1H, s); 6.88 (3H, m); 6.95 (1H, m); 7.15–7.34 (6H); 7.52 (1H, bd); 7.95 (1H, bd); 8.10 (1H, bs).

Diastereoisomer L: 1.04 and 1.05 (6H, 2s); 1.18 and 1.20 (6H, 2t); 2.37 (3H, s); 2.71 (2H, d); 2.79 (2H, d); 3.72 (2H, dd); 3.83 (3H, s); 3.90–4.24 (9H); 5.01 (1H, s); 6.88 (3H, m); 6.95 (1H, m); 7.15–7.34 (6H); 7.52 (1H, bd); 7.95 (1H, bd); 8.10 (1H, bs).

EXAMPLE 13

Preparation of methyl
1,4-dihydro-6-methyl-2-(N-methyl-N-(2-
(2-hydroxy-3-(2-methoxyphenoxy)-propylamino)-2-
methylpropyl)-aminomethyl)-4-(3-
nitrophenyl)-3,5-pyridinedicarboxylate A mixture of (–)-N-methyl-2-(2-hydroxy-3-(2-methoxyphenoxy)-propylamino)-2-methylpropylamine (6.4 g, 22.6 mmoles), methyl 2-chloromethyl-1,4-dihydro-6-methyl-4-(3-nitrophenyl)-3,5-pyridinedicarboxylate (9.6 g, 22.6 mmoles) and triethylamine (6.1 ml, 42.3 mmoles) in toluene is maintained at room temperature for 3 hours.

The reaction mixture is washed with water (100 ml), with a sature solution of potassium bicarbonate (75 ml) and with water (50 ml) again.

The organic phase is dried over sodium sulfate and filtered; the solvent is evaporated. The crude product is purified and the two diastereoisomers are separated by chromatography on silica gel (230–400 mesh) column; eluent, ethyl acetate:toluene:ammonium hydroxide= 90:10:1. The two diastereoisomer of methyl 1,4-dihydro-6-methyl-2-(N-methyl-N-(2-(2-hydroxy-3-(2-methoxyphenoxy)-propylamino)-2-methylpropyl)-aminomethyl)-4-(3-nitrophenyl)-3,5-pyridinedicarboxylate are thus obtained and then treated with a solution of hydrogen chloride gas in ethyl ether to give the corresponding dihydrochloride salts.

Diastereoisomer M: (greater Rf) (dihydrochloride), amorphous yellow solid; m.p.=138°–140° C.; (alpha)$_D$=−7.5 (c=0.5%, ethanol).

Diastereoisomer N: (lower Rf) (dihydrochloride), amorphous yellow solid; m.p.=134°–137° C.; (alpha)$_D$=−4.0 (c=0.5% ethanol).

Mass spectrum (chemical ionization, positive ions, ammonium hydroxide) m/e 627 (M+1)$^+$; 376; 335; 283; 238.

Diastereoisomer M:

$^1$H-NMR (free base) (300 MHz, CDCl$_3$): delta (ppm) 1.12 (6H, s); 2.40 (6H, s); 2.52 (2H, s); 2.76 (2H, m); 3.61 and 3.64 (6H, 2s); 3.83 (3H, s); 3.91 (2H, d); 3.96–4.10 (3H); 5.09 (1H, s); 6.84–6.98 (4H); 7.35 (1H, t); 7.61 (1H, bd); 7.96 (1H, bd), 8.09 (1H, bs).

Diastereoisomer N:

$^1$H-NMR (free base) (300 MHz, CDCl$_3$): delta (ppm) 1.11 and 1.13 (6H, 2 s); 2.38 (3H, s); 2.39 (3H, s); 2.53 (2H, dd); 2.78 (2H, m); 3.63 and 3.65 (6H, 2s); 3.84 (3H, s); 3.91 (2H, d); 3.95–4.10 (3H); 5.09 (1H, s); 6.84–6.98 (4H); 7.35 (1H, t); 7.61 (1H, bd); 7.96 (1H, dd); 8.09 (1H, bs).

Working in a similar way, the following compounds were prepared:

isopropyl 1,4-dihydro-6-methyl-2-(N-methyl-N-(2-(2-hydroxy-3-(2-methoxyphenoxy)-propylamino)-2-methylpropylaminomethyl)-4-(3-nitrophenyl)-3,5-pyridinedicarboxylate Diastereoisomer O: (greater Rf) (dihydrochloride), amorphous yellow solid; m.p.=150°–152° C.

Diastereoisomer P: (lower Rf) (dihydrochloride), amorphous yellow solid; m.p.=125°–128° C.

Mass spectrum (chemical ionization, positive ions, ammonium hydroxide) m/e 683 (M+1)$^+$; ; 238; 238.

Diastereoisomer O $^1$H-NMR (free base) (300 MHz, CDCl$_3$): delta (ppm) 1.08 (6H, 2d); 1.12 (6H, s); 1.25 (6H, d); 2.37 and 2.39 (6H, 2s); 2.52 (2H, s); 2.80 (2H, m); 3.84 (3H, s); 3.91 (2H, d); 3.98–4.10 (3H); 4.92 (2H, 2m); 5.05 (1H, s) 6.85–7.00 (4H); 7.35 (1H, t), 7.61 (1H, bd); 7.96 (1H, dd); 8.11 (1H, bs).

Diastereoisomer P $^1$H-NMR (free base) (300 MHz, CDCl$_3$): delta (ppm): 1.06–1.14 (12H); 1.24 and 1.26 (6H, 2s), 2.37 and 2.39 (6H, 2s); 2.51 (2H, s); 2.76 (2H, m); 3.84 (3H, s); 3.09 (2H, s); 3.98–4.10 (3H); 4.92 (2H, 2m), 5.04 (1H, s); 6.85–7.00 (4H); 7.33 (1H, t); 7.61 (1H, bd); 7.97 (1H, dd); 8.11 (1H, bs).

2-methoxyethyl 1,4-dihydro-6-methyl-2-(N-methyl-N-(2-(2-hydroxy-3-(2-methoxyphenoxy)-propylamino)-2-methylpropyl)-aminomethyl)-4-(3-nitrophenyl)-3,5-pyridinedicarboxylate Diastereoisomer Q: (greater Rf) (dihydrochloride), amorphous yellow solid; m.p.=125°–127° C.

Diastereoisomer R: (lower Rf) (dihydrochloride), amorphous yellow solid; m.p.=127°–128° C.

Mass spectrum (chemical ionization, positive ions, ammonium hydroxide) m/e 715 (M+1)$^+$; ; 283; 238.

Diastereoisomer Q $^1$H-NMR (free base) (300 MHz, CDCl$_3$): delta (ppm): 1.12 (6H, s); 2.39 (6H, s) 2.51 (2H, s), 2.77 (2H, m); 3.33 and 3.34 (6H, 2s); 3.54 (4H, m); 3.84 (3H, s); 3.90 (2H, d); 3.95–4.22 (7H); 5.11 (1H, s); 6.84–6.98 (4H); 7.34 (1H, t); 7.66 (1H, bd); 7.96 (1H, dd); 8.11 (1H, bs).

Diastereoisomer R $^1$H-NMR (free base) (300 MHz, CDCl$_3$): delta (ppm): 1.11 and 1.13 (6H, 2s), 2.39 (6H, s), 2.51 (2H, d); 2.75 (2H, m); 3.33 and 3.34 (6H, 2s); 3.54 (4H, m); 3.83 (3H, s); 3.90 (2H, s); 3.97–4.22 (7H); 5.11 (1H, s); 7.34 (1H, t); 7.67 (1H, bd); 7.97 (1H, dd); 8.11 (1H, bs).

methyl 1,4-dihydro-6-methyl-2-(N-methyl-N-(2-(2-hydroxy-3-(2-methoxyphenoxy)-propylamino)-2-methylpropyl)-aminomethyl)-4-(3-nitrophenyl)-5-carbethoxy-3-pyridinecarboxylate Diastereoisomer S: (greater Rf) (dihydrochloride), amorphous yellow solid; m.p.=120°–122° C.

Diastereoisomer T: (lower Rf) (dihydrochloride), amorphous yellow solid; m.p.=100°–102° C.

Mass spectrum (chemical ionization, positive ions, ammonium hydroxide) m/e 641 (M+1)$^+$; ; 238.

Diastereoisomer S $^1$H-NMR (free base) (300 MHz, CDCl$_3$): delta (ppm) 1.11 (6H, 1); 1.23 (3H, t), 2.36 and 2.37 (6H, 2s); 2.51 (2H, s); 2.75 (2H, m); 3.61 (3H, s); 3.74 (3H, s); 3.90 (2H, d); 3.95–4.15 (5H); 5.08 (1H, s); 6.85–7.00 (4H), 7.34 (1H, t); 7.61 (1H, bd); 7.96 (1H, dd); 8.10 (1H, bs).

Diastereoisomer T $^1$H-NMR (free base) (300 MHz, CDCl$_3$): delta (ppm) 1.11 and 1.13 (6H, 2s); 1.22 (3H, t); 2.36 and 2.38 (6H, 2s); 2.52 (2H dd); 2.75 (2H, m); 3.61 (3H, s); 3.84 (3H, s); 3.90 (2H, s); 3.96–4.15 (5H); 5.08 (1H, s); 6.85–7.00 (4H); 7.34 (1H, t); 7.61 (1H, bd), 7.96 (1H, dd); 8.10 (1H, bs)

ethyl 1,4-dihydro-6-methyl-2-(N-methyl-N-(2-(2-hydroxy-3-(2-methoxyphenoxy)-propylamino)-2-methylpropyl)-2-methylpropyl)-aminomethyl)-4-(3-nitrophenyl)-5-carboxymethyl-3-pyridinecarboxylate Diastereoisomer U: (greater Rf) (dihydrochloride), amorphous yellow solid; m.p.=139°–141° C.

Diastereoisomer V: (lower Rf) (dihydrochloride), amorphous yellow solid; m.p.=129°–132° C.

Mass spectrum (chemical ionization, positive ions, ammonium hydroxide) m/e 641 (M+1)$^+$; ; 611; 238.

Diastereoisomer U $^1$H-NMR (free base) (300 MHz, CDCl$_3$): delta (ppm) 1.12 (6H, s); 1.22 (3H, t), 2.38 (6H, s); 2.51 (2H, s); 2.78 (2H, m); 3.64 (3H, s); 3.84 (3H, s); 3.91 (2H, d); 3.95–4.15 (5H); 5.08 (1H, s); 6.84–6.98 (4H); 7.35 (1H, t); 7.61 (1H, d); 7.98 (1H, dd); 8.11 (1H, bs)

Diastereoisomer V $^1$H-NMR (free base) (300 MHz, CDCl$_3$): delta (ppm): 1.12 and 1.13 (6H, 2s); 1.22 (3H, t); 2.37 and 2.38 (6H, 2s); 2.53 (2H, ab); 2.70 (2H, m); 3.64 (3H, s); 3.83 (3H, s); 3.91

(2H, d); 3.96–4.12 (5H); 5.08 (1H, s); 6.84–7.00 (4H); 7.34 (1H, t); 7.61 (1H, bd); 7.98 (1H, dd); 8.11 (1H, bs).

ethyl 1,4-dihydro-6-methyl-2-(N-methyl-N-(2-(2-hydroxy-3-(2-methoxyphenoxy)-propylamino)-2-methylpropyl)-aminomethyl)-4-(2-trifluoromethyl)-3,5- pyridinedicarboxylate Diastereoisomer W: (greater Rf) (dihydrochloride), amorphous yellow solid; m.p.=117°–120° C.;

Diastereoisomer X: (lower Rf) (dihydrochloride), amorphous yellow solid; m.p.=113°–115° C.;

Mass spectrum (chemical ionization, positive ions, ammonium hydroxide) m/e 678 (M+1)$^+$;; 283; 238.

Diastereoisomer W $^1$H-NMR (free base) (300 MHz, CDCl$_3$): delta (ppm) 1.11 and 1.12 (6H, 2s); 1.16 and 1.17 (6H, 2t); 2.33 and 2.35 (6H, 2s); 2.50 (2H, s); 2.77 (2H, m); 3.84 (3H, s); 3.85 (2H, dd); 3.93–4.20 (7H); 5.60 (1H, bs); 6.86–7.00 (4H); 7.20 (1H, m); 7.37 (1H, bt); 7.46 (1H, bd); 7.51 (1H, bd).

Diastereoisomer X:

$^1$H-NMR (free base) (300 MHz, CDCl$_3$): delta (ppm) 1.11 and 1.12 (6H, 2s); 1.16 and 1.17 (6H, 2t); 2.50 (2H, s); 2.77 (2H, m); 3.84 (6H, s) 3.85 (2H, bs) 3.90–4.20 (7H); 5.60 (1H, bs); 6.85–7.00 (4H); 7.20 (1H, m) 7.36 (1H, bt); 7.46 (1H, dd); 7.51 (1H, bd).

ethyl 1,4-dihydro-6-methyl-2-(N-methyl-N-(2-(2-hydroxy-3-(2-methoxyphenoxy)-propylamino)-2-methylpropyl)-aminomethyl)-4-(2-chlorophenyl)-3,5- pyridinedicarboxylate Diastereoisomer Y: (greater Rf) (dihydrochloride), amorphous yellow solid; m.p.=115°–118° C.;

Diastereoisomer Z: (lower Rf) (dihydrochloride), amorphous yellow solid; m.p.=108°–110° C.;

Mass spectrum (chemical ionization, positive ions, ammonium hydroxide) m/e 644 (M+1)$^+$;; 238.

Diastereoisomer Y:

$^1$H-NMR (free base) (300 MHz, CDCl$_3$): delta (ppm) 1.11 (6H, s), 1.19 (6H, bt); 2.32 and 2.35 (6H, 2s); 2.50 (2H, s); 2.75 (2H, m); 3.83 (3H, s); 3.85 (2H, dd); 3.95–4.10 (7H); 5.40 (1H, s); 6.85–7.40 (8H).

Diastereoisomer Z:

$^1$H-NMR (free base) (300 MHz, CDCl$_3$): delta (ppm) 1.12 (6H, bs)); 1.19 (6H, t); 2.32 and 2.36 (6H, 2s); 2.51 (2H, s); 2.80 (2H, m); 3.83 (3H, s); 3.86 (2H, bs); 4.00–4.12 (7H); 5.40 (1H, s); 6.85–7.40 (8H).

ethyl 1,4-dihydro-6-methyl-2-(N-methyl-N-(2-(2-hydroxy-3-(2-methoxyphenoxy)-propylamino)-2-methylpropyl)-aminomethyl)-4-(2,3-dichlorophenyl)-3,5- pyridinedicarboxylate Diastereoisomer AA: (greater Rf) (dihydrochloride), amorphous yellow solid; m.p.=112°–114° C.;

Diastereoisomer AB: (lower Rf) (dihydrochloride), amorphous yellow solid; m.p.=118°–121° C.;

Mass spectrum (chemical ionization, positive ions, ammonium hydroxide) m/e 678 (M+1)$^+$;; 238.

Diastereoisomer AA:

$^1$H-NMR (free base) (300 Mhz, CDCl$_3$) delta (ppm) 1.11 (6H, bs); 1.18 (6H, 2t); 2.32 and 2.35 (6H, 2s); 2.50 (2H, s); 2.76 (2H, m); 3.84 (3H, s); 3.85 (2H, dd); 3.96–4.10 (7H); 5.47 (1H, s); 6.85–7.00 (4H); 7.03 (1H, t); 7.22 (1H, dd); 7.29 (1H, dd)

Diastereoisomer AB:

$^1$H-NMR (300 Mhz, CDCl$_3$): delta (ppm) 1.11 (6H, 2s); 1.18 (6H, 2t), 2.33 and 2.35 (6H, 2s); 2.50 (2H, s); 2.76 (2H, m), 3.84 (3H, s); 3.85 (2H, bs), 3.98–4.10 (7H); 5.46 (1H, s); 6.85–7.00 (4H), 7.02 (1H, t); 7.22 (1H, bd); 7.29 (1H, dd).

ethyl 1,4-dihydro-6-methyl-2-(N-methyl-N-(2-(2-hydroxy-3-(1-naphthoxy)-propylamino)-2-methylpropyl)-aminomethyl)-4- (3-nitrophenyl)-3,5-pyridinedicarboxylate Diastereoisomer AC: (greater Rf) (dihydrochloride), amorphous yellow solid; m.p.=128°–131° C.;

Diastereoisomer AD: (lower Rf) (dihydrochloride), amorphous yellow solid; m.p.=122°–125° C.;

Mass spectrum (chemical ionization, positive ions, ammonium hydroxide) m/e 675 (M+1)$^+$;; 643; 258.

Diastereoisomer AC:

$^1$H-NMR (free base) (300 MHz, CDCl$_3$): delta (ppm) 1.14 (6H, 2s); 1.19 (6H, 2t); 2.35 and 2.40 (6H, 2s); 2.54 (2H, s); 2.90 (2H, 2m), 3.92 (2H, dd); 4.00–4.22 (7H); 5.07 (1H, s); 6.80 (1H, d); 7.30–8.20 (10 H).

Diastereoisomer AD $^1$H-NMR (free base) (30 MHz, CDCl$_3$): delta (ppm) 1.15 (6H, 2s); 1.20 (6H, 2t); 2.36 and 2.40 (6H, 2s); 2.54 (2H, s); 2.90 (2H, 2m); 3.94 (2H, bd); 4.00–4.22 (7H); 5.08 (1H, s); 6.80 (1H, d), 7.30–8.20 (10H).

ethyl 1,4-dihydro-6-methyl-2-(N-methyl-N-(3-(2-hydroxy-3-(2-methoxyphenoxy)-propylamino)-3-methylbutyl)-aminomethyl)-4- (3-nitrophenyl)-3,5-pyridinedicarboxylate Diastereoisomers mixture (dihydrochloride), amorphous yellow solid;

Mass spectrum (chemical ionization, positive ions, isobutane) m/e 699 (M+1)$^+$;; 543.

$^1$H-NMR (free base) (300 Mhz, CDCl$_3$): delta (ppm) 1.12 and 1.20 (6H, 2s); 1.14–1.25 (6H); 1.60 and 1.72 (2H, 2 m); 2.32 and 2.33 (2H, 2s); 2.38 (3H, s); 2.65 (2H, m); 2.76 (1H, dd); 2.90 (1H, dd); 3.62–3.78 (2H); 3.83 (3H, 2s); 3.98–4.15 (7H); 5.09 and 5.11 (1H, 2s); 6.85–6.98 (4H); 7.35 (1H, bt); 7.60 (1H, bd); 7.98 (1H, dd); 8.10 (1H, m).

ethyl 1,4-dihydro-6-methyl-2-(N-methyl-N-(2-(2-hydroxy-3-(1-carbazolyloxy)-propylamino)-2-methylpropyl)-aminomethyl)-4- (3-nitrophenyl)-3,5-pyridinedicarboxylate Diastereoisomer AE: (greater RF) (dihydrochloride), amorphous yellow solid; m.p.=151°–154° C.;

Diastereoisomer AF: (lower Rf) (dihydrochloride), amorphous yellow solid; m.p.=149°–151° C.;

Mass spectrum (chemical ionization, positive ions, ammonium hydroxide) m/e 714 (M+1)$^+$;; 402; 378; 297; 184.

Diastereoisomer AE:

$^1$H-NMR (free base) (300 MHz, CDCl$_3$): delta (ppm) 1.16 (6H, bs); 1.20 (6H, 2t); 2.32 (3H, s); 2.39 (3H, s); 2.53 (2H, bs); 2.97 (2H, m); 3.91 (2H, dd); 4.00–4.34 (7H); 5.06 (1H, s); 6.66 (1H, d); 7.06 (1H, d); 7.15–7.44 (5H): 7.61 (1H, bs); 7.95 (1H, dd); 8.11 (1H, bs); 8.22 (1H, d).

Diastereoisomer AF:

$^1$H-NMR (free base) (300 MHz, CDCl$_3$): delta (ppm) 1.16 (6H, bs); 1.21 (6H, 2t), 2.34 (3H, s); 2.39 (3H, s); 2.54 (2H, bs); 2.98 (2H, m); 3.91 (2H, bs); 4.00–4.34 (7H); 5.08 (1H, s); 6.66 (1H, d); 7.06 (1H, d); 7.15–7.44 (5H); 7.61 (1H, bs); 7.95 (1H, dd); 8.11 (1H, bs); 8.22 (1H, d).

EXAMPLE 14

Preparation of Ethyl 1,4-dihydro-6-methyl-2-(N-acetyl-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate A mixture of ethyl 1,4-dihydro-6-methyl-2-(N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate (5 g; 5.6 mmoles), prepared according to example 9, acetic anhydride (0.53 ml; 5.6 mmoles), pyridine (0.45 ml; 5.6 mmoles) in toluene (50 ml) is kept at room temperature for two hours.

The reaction mixture is diluted with ethyl acetate (50 ml,) the organic phase is washed with water (30 ml), then with a potassium bicarbonate solution (40 ml) and eventually with water (30 ml).

After anhydrification of the organic extract with sodium sulfate and evaporation of solvent, the crude product is purified by chromatography on silica gel (230–400 mesh) column eluting with ethyl acetate:petroleum ether:ethanol:propylamine=100:100:0.5:1.

Chromatography pure Ethyl 1,4-dihydro-6-methyl-2-(N-acetyl-N-(2-((2-hydroxy-3-(2-methoxyphenoxy)-propyl)-triphenylmethylamino)-2-methylpropyl)-aminomethyl)-4-(3-nitrophenyl)-3,5-pyridinecarboxylate is thus obtained (thin layer chromatography; eluent, CH$_2$Cl$_2$:methanol:NH$_3$OH=98:4:0,2).

Mass spectrum (chemical ionization, positive ions, ammonium hydroxide): m/e 681 (M—CPh$_3$)$^+$; 342; 243.

IR (CHCl$_3$): characteristic bands at 3300, 3200, 1700, 1650, 1600, 1530, 1500 (cm$^{-1}$).

Working in a similar way but using benzoyl chloride, isobutyryl chloride, ethyl chlorocarbonate and methane sulfonyl chloride as acylating agents, the following compounds were prepared:

Ethyl 1,4-dihydro-6-methyl-2-(N-benzoyl-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate IR (CHCl$_3$): characteristic bands at 3300, 3200, 1690, 1640, 1600, 1530, 1500 (cm$^{-1}$).

Ethyl 1,4-dihydro-6-methyl-2-(N-(1-oxo-2-methylpropyl)-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate Mass spectrum (chemical ionization, positive ions, isobutane): m/e 953 (M+1)$^+$; 710; 458; 342; 243.

IR (CHCl$_3$): bands at 3300, 3220, 1690, 1640, 1600, 1530, 1500 (cm$^{-1}$).

Ethyl 1,4-dihydro-6-methyl-2-(N-ethoxycarbonyl-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate Mass spectrum (chemical ionization, negative ions, isobutane): m/e 955 (M+1)$^-$; 909; 666; 372; 342.

IR (CHCl$_3$); characteristic bands at 3300, 3200, 1690, 1640, 1600, 1530, 1500 (cm$^{-1}$).

Ethyl 1,4-dihydro-6-methyl-2-(N-methylsulfonyl-N-(2-((2-hydroxy-3-(2-methoxyphenoxy)-propyl)-triphenylmethylamino)-2-methylpropyl)-aminomethyl)-4-(3-nitrophenyl)-3,5-pyridinedicarboxylate Mass spectrum (chemical ionization, negative ions, isobutane): me/ 881 (M—CH$_3$SO$_2$)$^-$; 718; 638; 401; 372; 243.

IR (CHCl$_3$): characteristic bands at 3320, 3200, 1690, 1650, 1630, 1600, 1530, 1500, (cm$^{-1}$).

EXAMPLE 15

Preparation of Ethyl 1,4-dihydro-6-methyl-2-(N-acetyl-N-(2-(2-hydroxy-3-(2-methoxyphenoxy)-propylamino)-2-methylpropyl)-aminomethyl)-4-(3-nitrophenyl)-3,5-pyridinedicarboxylate Concentrate HCl (29 ml) is added to a solution of Ethyl 1,4-dihydro-6-methyl-2-(N-acetyl-N-(2-((2-hydroxy-3-(2-methoxyphenoxy)-propyl)triphenylmethylamino)-2-methylpropyl)-aminomethyl)-4-(3-nitrophenyl)-3,5-pyridinecarboxylate (14.4 g; 15.6 mmoles), prepared as disclosed in example 14, in tetrahydrofuran (150 ml).

After half an hour at room temperature, the solvent is evaporated.

The crude product is extracted with methylene chloride and an aqueous solution of potassium bicarbonate; the organic phase is washed with water and dried over sodium sulfate.

After evaporation of the solvent, the crude product is purified by chromatography on a silica gel column (230–400 mesh) eluting with methylene chloride:methanol:NH$_4$OH= 100:5:0.5.

Ethyl 1,4-dihydro-6-methyl-2-(N-acetyl-N-(2-(2-hydroxy-3-(2-methoxyphenoxy)-propylamino)-2-methylpropyl)-aminomethyl)-4-(3-nitrophenyl)- 3,5-pyridinedicarboxylate is thus obtained in the form of a yellow oil chromatographycally pure (thin layer chromatography; eluent, CH$_2$Cl$_2$:methanol:NH$_4$OH=100:5:0.5). Hydrochloride: amorphous solid; p.f.=98°–100° C.

Mass spectrum (chemical ionization, positive ions, isobutane): m/e 683 (M+1)$^+$; 665; 648; 575; 508.

$^1$H-NMR (free base) (300 MHz, CDCl$_3$): delta (ppm): 1.15–1.25 (12H); 2.05–2.43 (6H, 5s); 2.85 (2H, m); 3.40 (2H, m); 3.82 and 3.84 (3H, 2s); 5.08–5.13 (2H); 6.85–7.00 (4H, m); 7.36 (1H, m), 7.62 (1H, m); 7.98 (1H, m); 8.10 (1H, m).

Working in a similar way, the following compounds were prepared:

Ethyl 1,4-dihydro-6-methyl-2-(N-benzoyl-N-(2-(2-hydroxy-3-(2-methoxyphenoxy)-propylamino)-2-methylpropyl)-aminomethyl)-4-(3-nitrophenyl)-3,5-pyridinedicarboxylate hydrochloride Mass spectrum (chemical ionization, negative ions, ammonium hydroxide): m/e 745 (M+1)$^-$; 727; 374; 342.

$^1$H-NMR (free base) (300 MHz, CDCl$_3$): delta (ppm): 0.9–1.3 (12H); 1.6 (3H, bs); 3.25 (2H, m); 3.82 and 3.83 (3H, 2s); 5.10–5.50 (3H); (6.80–7.00 (4H, m).

Ethyl 1,4-dihydro-6-methyl-2-N-(1-oxo-2-methylpropyl)-N-(2-(2-hydroxy-3-(2-methoxyphenoxy)-propylamino)-2-methylpropyl)-aminomethyl)-4-(3-nitrophenyl)-3,5-pyridinedicarboxylate hydrochloride Mass spectrum (chemical ionization, positive ions, isobutane): m/e 711 (M+1)$^+$; 460; 321; 238.

$^1$HNMR (free base) (300 MHz, CDCl$_3$): delta (ppm): 0.96–1.25 (18H); 2.24–2.32 (3H, 3s); 3.10 (1H, m); 3.38 (2H, m); 3.81 and 3.83 (3H, 2s); 5.08–5.16 (3H); 6.90 (4H, m); 7.35 (1H, m); 7.60 (1H, bd); 7.98 (1H, m); 8.10 (1H, bs).

Ethyl 1,4-dihydro-6-methyl-2-(N-ethoxycarbonyl-N-(2-(2-hydroxy-3-(2-methoxyphenoxy)-propylamino)-2-methylpropyl)-aminomethyl)-4-(3-nitrophenyl)-3,5-pyridinedicarboxylate hydrochloride Mass spectrum (chemical ionization, negative ions, ammonium hydroxide): m/e 711 (M−1)$^-$; 666; 342.

$^1$HNMR (free base) (300 MHz, CDCl$_3$): delta (ppm): 1.10–1.30 (15H); 2.28–2.40 (3H, m); 2.80 (2H, m); 3.35 (2H, m); 3.82 and 3.84 (3H, 2s); 5.10 (1H, d); 6.90 (4H, m); 7.35 (1H, bt); 7.62 (1H, bd); 7.98 (1H, bd); 8.11 (1H, m).

Ethyl 1,4-dihydro-6-methyl-2-(N-methylsulfonyl-N-(2-(2-hydroxy-3-(2-methoxyphenoxy)-propylamino)-2-methylpropyl)-aminomethyl)-4-(3-nitrophenyl)-3,5-pyridinedicarboxylate hydrochloride Mass spectrum (chemical ionization, negative ions, isobutane): m/e 718 (M)$^-$; 639; 372; 345.

$^1$H-NMR (free base) (300 MHz, CDCl$_3$); delta (ppm): 1.15–1.25 (12H); 2.38 and 2.40 (3H, 2s); 2.80 (2H, m); 3.00 (3H, bs); 3.19 (2H, m); 3.83 and 3.84 (3H, 2s); 4.56 (1H, dd); 4.88 (1H, d); 5.10 (1H, d); 6.90 (4H; 7.37 (1H, t); 7.66 (1H, bd); 7.98 (1H, bd); 8.12 (1H, bs).

EXAMPLE 16

Evaluation of the Pharmacological Activity in vitro

Calcium-antagonist activity of the compounds of formula I has been tested as capability of antagonizing the effect of Ca$^{++}$ submaximal concentrations (3 mM) on preparations of rabbit mesenteric artery in Krebs depolarizer, prepared according to Towart "J. Cardiovasc. Pharmacol. 4, 895, (1982)".

The compounds of this invention, tested as calcium antagonist agents on the rabbit mesenteric artery show an IC$_{50}$ of from 10 to 200 (nM); Ki affinity for beta$_1$ receptors is of from 30 to 2000 (nM) and for beta$_2$ receptors is of from 20 to 5000 (nM).

By way of example, IC$_{50}$ of some compounds of formula I are given in the following table 1.

TABLE 1

| rabbit mesenteric artery test | |
|---|---|
| Compound | IC$_{50}$ (nM) |
| Compound 1 | 47 |
| diastereoisomer A | 15 |
| diastereoisomer B | 120 |

Moreover, the beta-blocking activity has been tested by means of the binding test both towards beta$_1$ heart receptors and towards beta$_2$ lung receptor in mouse according to the methods described in the J. Biol. Chem., 253, 5090, (1978) and in the Br. J. Pharmacol., 68, 57, (1980).

The compounds of formula I showed a greater affinity towards beta$_1$ receptors than towards beta$_2$ receptors.

By way of example, in table 2 the receptorial affinity data as Ki (nM) for some compounds of formula I are given.

TABLE 2

| | Receptorial affinity | |
|---|---|---|
| Compound | Ki (nM) rat heart beta$_1$ receptors | Ki (nM) rat Lung beta$_2$ receptors |
| diastereoisomer A | 600 | 2050 |
| diastereoisomer B | 165 | 560 |
| atenolol | 840 | 18000 |

Pharmacological Activity in vivo

The compounds of formula I produce antihypertensive effects in rat and dog with concomitant reduction of the heart rate.

For example, in the anesthetized dog, compound 1 caused a heart rate reduction of from 9 to 23% and a reduction of the mean arterial pressure of from 3 to 15% at doses of from 100 to 400 ug/kg; at the same doses diastereoisomer A caused a heart rate reduction of from 17 to 30% and a mean arterial pressure reduction of from 12 to 25%, respectively. Both hypotensive effect and bradycardia proved to be particularly durable, lasting over five hours.

We claim:

1. A compound of the formula

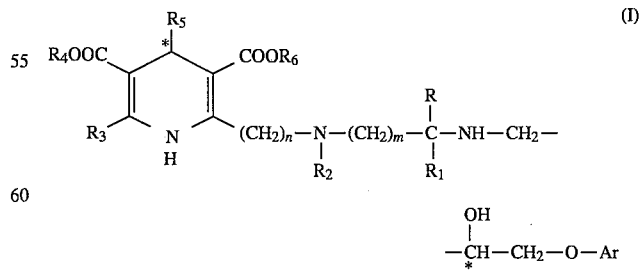

wherein

Ar is an optionally substituted mono- or dicyclo aromatic or heteroaromatic ring system, having at most 10 ring atoms, any heteroaromatic ring having at least 5 ring atoms, any substituent of a substituted ring system being a member selected from the group consisting of halogen, hydroxy, $C_1$–$C_5$ alkyl, $C_2$–$C_5$ alkenyl, $C_1$–$C_3$ alkoxy, allyloxy, alkoxyalkyl having from 1 to 5 carbon atoms in each of the alkyl and alkoxy moieties and optional unsaturation in the chain, phenoxy, phenylalkoxy, aminocarbonylalkyl having from 1 to 3 carbon atoms in the alkyl moiety, cyano, carboxy, carbamoylalkyl, aminocarboxy, amino, mono-alkylamino and dialkylamino wherein the nitrogen atom is optionally a ring member;

each of R and $R_1$ is, independently, hydrogen or $C_1$–$C_3$ alkyl;

$R_2$ is a straight-chain or branched unsubstituted or aryl-substituted $C_1$–$C_7$ alkyl, straight-chain or branched unsubstituted or aryl-substituted $C_2$–$C_7$ alkenyl, or X—$R_7$, where X is CO, CS or $SO_2$, and $R_7$ is alkyl or alkoxyalkyl having from 1 to 5 carbon atoms in each of the alkyl and alkoxy moieties, hydroxy, $C_1$–$C_3$ alkoxy, phenyl, mono-alkylamino or di-alkylamino having from 1 to 5 carbon atoms in each alkyl moiety or $C_1$–$C_5$ alkylthio;

$R_3$ is cyano, amino or optionally-fluoro-substituted $C_1$–$C_3$ alkyl;

each of $R_4$ and $R_6$ is, independently, alkyl or alkoxyalkyl having from 1 to 5 carbon atoms in each alkyl and alkoxy moiety;

$R_5$ is an optionally-substituted ring selected from the group consisting of phenyl, napthyl, tetrahydronaphthyl and indanyl, wherein any ring substituent is a member selected from the group consisting of halogen, hydroxy, alkyl, alkenyl, alkoxy, alkenyloxy, alkoxyalkyl, alkanoyl, trifluoromethyl, amino, nitro, carbamoyl, cyano, alkylthio, carbamoylalkyl and alkanoylamino having up to six carbon atoms in the alkyl moiety;

each of m and n is, independently, 1, 2 or 3;

or a salt thereof with an organic or inorganic pharmaceutically-acceptable acid.

2. A compound according to claim 1, wherein Ar is an optionally-substituted monocyclic or bicyclic ring selected from the group consisting of phenyl, naphthyl, isobenzofuranyl, benzofuranyl, 3,4-dihydrocarbostyryl, benzopyranyl, tetrahydronaphthyl, carbazolyl, indenyl, indolyl and 1,2,5-thiadiazolyl, and any ring substituent is a member selected from the group consisting of fluorine, chlorine, bromine, acetyl, allyl, carbamoylmethyl, butyroylamino, cyclohexyl, cyano, hydroxy, butyroyl, acetylamino, methoxycarbonyl, methoxyethyl, methoxy, allyloxy, cyclopentyl, cyclopropyl, morpholine, ethyl and isobutyroyl.

3. A compound according to claim 1, wherein

Ar is a member selected from the group consisting of 2-methoxyphenyl, 2-allyloxyphenyl, 2-cyanophenyl, 2-methylphenyl, 2-allylphenyl, 4-carbamoylmethylphenyl, 4-hydroxyphenyl, 4-morpholino-1,2,5-thiadiazol-3-yl,indol-4-yl and 3,4-dihydro-1(H)-carbostyryl-5-yl;

each of R and $R_1$ is, independently, hydrogen or methyl;

$R_2$ has its previously-ascribed meaning;

$R_3$ is methyl or trifluoromethyl;

$R_5$ is substituted phenyl, any substituent of which is a member selected from the group consisting of nitro, trifluoromethyl and halogen;

X is a carbonyl or sulfonic group; and $R_7$ is methyl, ethyl, isopropyl, phenyl, dimethylamino, diethylamino, methoxy or ethoxy.

4. A compound of claim 1 wherein $R_3$ is cyano.

5. A compound of claim 1 wherein $R_3$ is amino.

6. A compound of claim 1 wherein $R_3$ is $C_1$–$C_3$ alkyl.

7. A compound of claim 1 wherein $R_3$ is fluoro-substituted $C_1$–$C_3$ alkyl.

8. A compound of the formula $$R_4OOC \overset{R_5}{\underset{*}{\diagdown}} COOR_6$$
$$R_3 \diagup N \diagdown (CH_2)_n-N-(CH_2)_m-\overset{R}{\underset{R_1}{C}}-NH-CH_2-$$
$$\phantom{xxxxxxxxx} H \phantom{xxxx} R_2$$

$$-\overset{OH}{\underset{*}{CH}}-CH_2-O-Ar$$

(I)

wherein

Ar is a member selected from the group consisting of phenyl, naphthyl, isobenzofuranyl, benzofuranyl, 3,4-dihydrocarbostyryl, benzopyranyl, tetrahydronaphthyl, carbazolyl, indenyl, indolyl and 1,2,5-thiadiazolyl optionally substituted by fluorine, chlorine, bromine, acetyl, allyl, carbamoylmethyl, butyroylamino, cyclohexyl, cyano, hydroxy, butyroyl, acetylamino, methoxycarbonyl, methoxyethyl, methoxy, allyloxy, cyclopentyl, cyclopropyl, morpholine, ethyl or isobutyroyl;

each of R and $R_1$ is, independently, hydrogen or $C_1$–$C_3$ alkyl;

$R_2$ is optionally-aryl-substituted straight or branched $C_1$–$C_7$ alkyl, optionally-aryl-substituted straight or branched $C_2$–$C_7$ alkenyl, or X—$R_7$, where X is CO, CS or $SO_2$, and $R_7$ is alkyl or alkoxyalkyl having from 1 to 5 carbon atoms in each alkyl and alkoxy moiety, hydroxy, $C_1$—$C_3$ alkoxy, mono- or di-alkylamino having from 1 to 5 carbon atoms in each alkyl moiety, or $C_1$–$C_5$ alkylthio;

$R_3$ is cyano, amino or optionally-fluoro-substituted $C_1$–$C_3$ alkyl;

each of $R_4$ and $R_6$ is, independently, alkyl or alkoxyalkyl having from 1 to 5 carbon atoms in each of the alkyl and alkoxy moieties;

$R_5$ is optionally-ring-substituted phenyl, naphthyl, tetrahydronaphthyl or indanyl, wherein any ring substituent is a member selected from the group consisting of halogen, hydroxy, alkyl, alkenyl, alkoxy, alkenyloxy, alkoxyalkyl, alkanoyl, trifluoromethyl, amino, nitro, carbamoyl, cyano, alkylthio, carbamoylalkyl and alkanoylamino having up to 6 carbon atoms in the alkyl moiety;

each of m and n is, independently, 1, 2 or 3;

or a salt thereof with an organic or inorganic pharmaceutically-acceptable acid.

9. A compound according to claim 1, wherein

Ar is a member selected from the group consisting of 2-methoxyphenyl, 2-allyloxyphenyl, 2-cyanophenyl, 2-methylphenyl, 2-allylphenyl, 4-carbamoylmethylphenyl, 4-hydroxyphenyl, 4-morpholino-1,2,5-thiadiazol-3-yl, indol-4-yl and 3,4-dihydro-1(H)-carbostyryl-5-yl;

each of R and $R_1$ is, independently, hydrogen or methyl;

$R_2$ is optionally-aryl-substituted straight or branched $C_1$–$C_7$ alkyl, optionally-aryl-substituted straight or branched $C_2$–$C_7$ alkenyl, or X—$R_7$, where X is a carbonyl or a sulfonic group, and $R_7$ is methyl, ethyl, isopropyl, phenyl, dimethylamino, diethylamino, methoxy or ethoxy;

$R_3$ is methyl or trifluoromethyl; and $R_5$ is a substituted phenyl where any substituent is a member selected from the group consisting of nitro, trifluoromethyl and halogen.

10. A compound of claim 8 wherein $R_3$ is cyano.

11. A compound of claim 8 wherein $R_3$ is amino.

12. A compound of claim 8 wherein $R_3$ is $C_1$–$C_3$ alkyl.

13. A compound of claim 8 wherein $R_3$ is fluoro-substituted $C_1$–$C_3$ alkyl.

14. A compound of claim 1 wherein

Ar is a member selected from the group consisting of 2-methoxyphenyl, 2-allyloxyphenyl, 2-cyanophenyl, 2-methylphenyl, 2-allylphenyl, 4-carbamoylmethylphenyl, 4-hydroxyphenyl, 4-morpholino-1,2,5-thiadiazol-3-yl, indol-4-yl and 3,4-dihydro-2(H)-carbostyryl-5-yl;

each of R and $R_1$ is, independently, hydrogen or $C_1$–$C_3$ alkyl;

$R_2$ is optionally-aryl-substituted straight or branched $C_1$–$C_7$ alkyl, optionally-aryl-substituted straight or branched $C_2$–$C_7$ alkenyl, or X—$R_7$, where X is CO, CS or $SO_2$, and $R_7$ is alkyl or alkoxyalkyl having from 1 to 5 carbon atoms in each of the alkyl and alkoxy moieties, hydroxy, $C_1$–$C_3$ alkoxy, monoalkylamino or dialkylamino having from 1 to 5 carbon atoms in each alkyl moiety, or $C_1$–$C_5$ alkylthio;

$R_3$ is cyano, amino or optionally-fluoro-substituted $C_1$–$C_3$ alkyl;

each of $R_4$ and $R_6$ is, independently, alkyl or alkoxyalkyl having from 1 to 5 carbon atoms in each alkyl and alkoxy moiety;

$R_5$ is optionally-substituted ring selected from the group consisting of phenyl, naphthyl, tetrahydronaphthyl and indanyl, wherein any substituent of a substituted ring is a member selected from the group consisting of halogen, hydroxy, alkyl, alkenyl, alkoxy, alkenyloxy, alkoxyalkyl, alkanoyl, trifluoromethyl, amino, nitro, carbamoyl, cyano, alkylthio, carbamoylalkyl and alkanoylamino having up to 6 carbon atoms in the alkyl moiety;

each of m and n is, independently, 1, 2 or 3;

or a salt thereof with an organic or inorganic pharmaceutically-acceptable acid.

15. A compound of claim 14, wherein each of R and $R_1$ is, independently, hydrogen or methyl;

$R_2$ is optionally-aryl-substituted straight or branched $C_1$–$C_7$ alkyl, optionally-aryl-substituted straight or branched $C_2$–$C_7$ alkenyl, or X—$R_7$, where X is a carbonyl or a sulfonic group, and $R_7$ is methyl, ethyl, isopropyl, phenyl, dimethylamino, diethylamino, methoxy or ethoxy;

$R_3$ is methyl or trifluoromethyl; and $R_5$ is phenyl optionally substituted by nitro, trifluoromethyl or halogen.

16. A pharmaceutical composition useful for treating vasospastic, angina, hypertension and vasoconstriction pathologies, containing an effective amount of a compound of claim 1 together with a pharmaceutical excipient.

17. A pharmaceutical composition useful for treating vasospastic, angina, hypertension and vasoconstriction pathologies, containing an effective amount of a compound of claim 8 together with a pharmaceutical excipient.

18. A pharmaceutical composition useful for treating vasospastic, angina, hypertension and vasoconstriction pathologies, containing an effective amount of a compound of claim 14 together with a pharmaceutical excipient.

19. A compound of claim 1 wherein Ar is an optionally-substituted member selected from the group consisting of phenyl, naphthyl, isobenzofuranyl, benzofuranyl, 3,4-dihydrocarbostyryl, benzopyranyl, tetrahydronaphthyl, carbazolyl, indenyl, indolyl and 1,2,5-thiadazolyl.

* * * * *